United States Patent
Mori et al.

(10) Patent No.: US 6,984,655 B1
(45) Date of Patent: *Jan. 10, 2006

(54) PHOTODYNAMIC THERAPY FOR SELECTIVELY CLOSING NEOVASA IN EYEGROUND TISSUE

(75) Inventors: Keisuke Mori, Saitama (JP); Shin Yoneya, Saitama (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/203,420

(22) PCT Filed: Feb. 17, 2000

(86) PCT No.: PCT/JP00/00901

§ 371 (c)(1),
(2), (4) Date: Oct. 24, 2002

(87) PCT Pub. No.: WO01/60360

PCT Pub. Date: Aug. 23, 2001

(51) Int. Cl.
*A61K 31/40* (2006.01)

(52) U.S. Cl. .................. 514/410; 600/431; 604/20
(58) Field of Classification Search ............. 514/410; 600/431; 604/20
See application file for complete search history.

(56) References Cited

U.S. PATENT DOCUMENTS 5,633,275 A * 5/1997 Mori et al. ............... 514/410
6,128,524 A * 10/2000 Yoneya et al. ............ 600/431
RE37,180 E      5/2001 Mori et al.

OTHER PUBLICATIONS

K. Mori et al., "Angiographic and Histologic Effects of Fundus Photodynamic Therapy with a Hydrophilic Sensitizer (Mono-L-Aspartyl Chlorin e6)", Ophthalmology 1999, vol. 106, pps. 1384-1391.*

* cited by examiner

*Primary Examiner*—Kevin E. Weddington
(74) *Attorney, Agent, or Firm*—B. Aaron Schulman; Stites & Harbison PLLC

(57) ABSTRACT

A method is provided for selectively occluding neovascular vessels formed in the ocular fundus of an eye, which includes intravenously administering a mono-L-aspartyl chlorin compound to a patient; subsequently estimating an appropriate time point when the mono-L-aspartyl chlorin compound has decreased in its concentration or has been eliminated from the retinal normal vascular vessels of the patient but is still remaining at an appropriate concentration in the vascular walls of the neovascular vessels of the ocular fundus; irradiating a laser light at a 664 nm-wavelength which is initiated at the appropriate time; and using the irradiation of the laser light to target lesions comprising the neovascular vessels, at a controlled power.

38 Claims, No Drawings

US 6,984,655 B1

PHOTODYNAMIC THERAPY FOR SELECTIVELY CLOSING NEOVASA IN EYEGROUND TISSUE

TECHNICAL FIELD

This invention relates to photodynamic therapy methods for occluding selectively such neovascular vessels as formed in the ocular fundus of eye, without involving any damage or impairment in the normal vascular vessels present in the tissues of the ocular fundus. More specifically, this invention relates to photodynamic therapy methods for occluding exclusively the choroidal neovascular vessels and/or retinal neovascular vessels, without damaging or impairing the retinal normal parenchymal tissue, the retinal normal vascular vessels and/or the choroidal normal vascular vessels of eye, which methods each comprises intravenously administering mono-L-aspartyl chlorin e6 tetra-sodium salt to a mammalian animal having the choroidal neovascular vessels and/or retinal neovascular vessels, and then starting to irradiate a laser light of 664 nm-wavelength to the lesions comprising the neovascular vessels in the ocular fundus at a certain designated fluence of the laser light and at a such time point which is chosen and designated cautiously and ingeniously.

Furthermore, this invention also relates to a novel pharmaceutical composition for use in a photodynamic therapy method as mentioned above, which is in the form of a single dosage unit for intravenous injection. It is well known that the choroidal neovascular vessels are formed in patients with age-related macular degeneration and that the retinal neovascular vessels are formed in patients with proliferative diabetic retinitis.

BACKGROUND OF THE ART

It is well known that photodynamic therapy or photochemotherapy is a therapeutic method which comprises administering a photosensitizer to a patient having pathological lesions, followed by irradiating a light of a wavelength active to excite the photosensitizer, to the pathological lesions where the administered photosensitizer has accumulated.

In a method of photodynamic therapy (abbreviated as PDT hereinafter) which is applied to the therapeutic treatment of cancer or tumor, there is administered such a photosensitizer which is capable of accumulating in the cancer or tumor tissue, particularly in the endothelial cell layers of the neovascular vessels present in the cancer or tumor tissue. Subsequently, the cancer tissue or the vascular walls containing the photosensitizer accumulated therein is irradiated with an exciting laser light active to excite photochemically the photosensitizer, so that the thus excited photosensitizer can further excite the oxygen molecules present in the surrounding regions around the photosensitizer. Through the excitation of the oxygen molecules, singlet oxygen (active oxygen) can be generated. Due to the cytotoxicity of the singlet oxygen, the cancer or tumor cells and the endothelial cells of the neovascular vessels containing the excited photosensitizer can be necrosed.

At an early development stage of PDT, hematoporphyrin derivatives such as photofrin, rose bengal and others were used as first-generation photosensitizers. The first-generation photosensitizers for use in PDT had such drawbacks that they have a poor selectivity to accumulate in the target tumor cells while they can readily accumulate in the normal cells, and that the first-generation photosensitizers can additionally involve a long-term phototoxicity in the skin of the patients [see, for example, Cancer Res., Vol. 38, pp. 2628–2635 (1978); and Cancer Res., Vol. 52, pp. 924–930 (1992)].

In recent years, the second-generation photosensitizers have been developed for PDT of cancer. Benzoporphyrin derivatives, mono-L-aspartyl chlorin e6 and others have been known as the second-generation photosensitizers [see, for example, a report of Kessel et al., entitled "Photodynamic therapy and bio-medical lasers", pp. 526–530 (1992), Elsevier Science Publishers, Co., Amsterdam; and a report of Nelson et al., Cancer Res., Vol. 47, pp. 4681–4685 (1987)]. Mono-L-aspartyl chlorin e6 is one of the known fluorescent tetrapyrrol derivatives. The properties of mono-L-aspartyl chlorin e6 which is present in the cells in vivo have been examined in detail by W. G. Roberts [see a report of W. G. Roberts, entitled "Role of Neovasculature and Vascular Permeability on the Tumor Retention of Photodynamic Agents", Cancer Res., Vol. 52, pp. 924–930 (1992)]. Based on the experiments of W. G. Roberts et al., with using chicken chorioallantoic membrane (abbreviated as CAM hereinafter) which is a tissue formed of the differentiation-type neovascular vessels of fertilized chicken egg, it was reported that the property of a photosensitizer to be selectively uptaken in the cancer cells and be accumulated therein can vary depending on the sort of the photosensitizer. In the above-mentioned reports, it is stated that mono-L-aspartyl chlorin e6 possesses a significantly higher selectivity to accumulate in the cancer cells, as compared with chlorin e6 and uro-porphyrin. Mono-L-aspartyl chlorin e6 or a salt thereof is able to absorb well a light of 664 nm-wavelength which is permeable deeply into animal tissue, so that the mono-L-aspartyl chlorin e6 compound can be photo-excited well in vivo after administration thereof. Additionally, it has been confirmed from some experiments with mice that mono-L-aspartyl chlorin e6 or a salt thereof can be metabolized and be cleared or eliminated from a living body of the host animal at a clearance speed of 10 times higher or more than that of the previously known hematoporphyrin derivatives, and that the concentration of mono-L-aspartyl chlorin e6 present in the plasma can decrease to a concentration of $\frac{1}{100}$-fold of the initial concentration thereof in 10 hours after the first time of the intravenous administration of mono-L-aspartyl chlorin e6 [see the report of Kessel, et al., supra., entitled "Photodynamic therapy and Biomedical lasers", pp. 526–530 (1992)]; and a report of C. J. Gomer and A. Ferrario et al., Cancer Res., Vol. 50, pp. 3985–3990 (1990)].

The above-mentioned experiments made by W. G. Roberts et al., with using chicken chorioallantoic membrane (CAM) have revealed that mono-L-aspartyl chlorin e6 tetra-sodium salt is able to be more selectively uptaken and accumulated at a higher concentration in the actively growing cells of the neovascular vessels in CAM, than such concentration at which the mono-L-aspartyl cholorin e6 salt can be uptaken and accumulated in the cells of the normal vascular vessels.

It has been indicated that mono-L-aspartyl chlorin e6 or a salt thereof has further characteristic properties that it is able to bind readily to the blood albumin and is hardly diffused in the normal tissue or normal vascular vessels having barriers, because mono-L-aspartyl chlorin e6 or a salt thereof has a low lipophilicity, and that the intracellular migration of the mono-L-aspartyl chlorin e6 compound will occur not through the physical diffusion but through the cellular endocytosis or cellular absorption.

Incidentally, Japanese Patent Publications Nos. 88902/1994 and 89000/1994 as well as their corresponding U.S.

Pat. Nos. 4,675,338 and 4,693,885 describe, for example, mono-L-aspartyl chlorin e6 and mono-L-glutamyl chlorin e6 or salts thereof. And, these patents mentioned above describe also that the tetrapyrrol derivatives may be used as a photosensitizer for diagnosis and therapeutic treatment of tumor. In the aforementioned Japanese patents and USA patents, it is described that a fluorescent tetrapyrrol derivative which has been accumulated in the tumor tissue after the administration thereof can be photo-excited by irradiation of a potent light such as laser beam, so that the tetrapyrrol derivative so photo-excited can exert a necrotic action on the tumor cells.

There are known some experiments where the choroidal neovascular vessels of a monkey eye were destroyed by PDT with using rose bengal as a photosensitizer [Arch. Ophthalmol., Vol. 111, June/1993, pp. 855–860]. There are known additional experiments where the choroidal neovascular vessels of a monkey eye were occluded by PDT with using benzoporphyrin derivative mono-acid (Verteporfin as the photosensitizer) [Arch. Ophthalmol., Vol. 113, June/1995, pp. 810–818].

Furthermore, U.S. Pat. Nos. 5,705,518 and 5,770,619 of Richer et al., describe a PDT experiment where a photosensitizer, benzoporphyrin derivative mono-acid ring A (BPD-MA) is prepared as its liposome and is intravenously administered to a mouse having transplanted M-1 tumor, followed by irradiating an exciting laser beam to the mouse. Based on these experiments of Richter et al, there is proposed a method for destroying or impairing an area of neovascularization, which comprises transcutaneously irradiating said area with a laser light before an administered photosensitizer has permeated into dermal tissue or other normal tissues, so that the dermal phototoxicity can be avoided. In these patents of U.S. Pat. Nos. 5,705,518 and 5,770,619, Richter et al. refer to mono-L-aspartyl chlorin e6 as one example of the photosensitizer, and they additionally refer to that the method as proposed by Richer et al is possible to be applied to the destruction or impairment of the area of neovascularization as formed in the eye. However, there is nowhere disclosed any experimental Example which to show that any practical application of the method of Richer et al. was made to the field of ophthalmology.

The present inventors, namely Dr. Mori and Dr. Yoneya et al., previously proposed a method for photochemotherapeutically occluding neovascular vessels in the ocular fundus, and this proposed method was based on the results of their experiments wherein the normal vascular vessels in the ocular fundus of a normal pigmented rabbit were occluded, when the PDT with mono-L-aspartyl chlorin e6 tetra-sodium salt as a photosensitizer was applied to the normal vascular vessels (see U.S. Pat. No. 5,633,275). Furthermore, Dr. Mori and Dr. Yoneya et al., have carried out some experiments in which there are diagnosed such impairment of the retina and such occlusion of choroidal normal vascular vessel which had been involved when the PDT with mono-L-aspartyl chlorin e6 tetra-sodium salt as a photosensitizer was applied to the choroidal normal vascular vessels in the eye of Japanese monkey, with irradiating a laser light of 664 nm-wavelength at a fluence of 7.5 J/cm$^2$ or less [Ophthalmology, Vol. 106, No. 7, pp. 1384–1391 (July, 1999)].

On the other hand, it is known that the neovascularization occurring in the ocular fundus tissue can severely damage the visual functions. For example, the choroidal neovascularization as involved by the age-related macular degeneration is a major cause for the intermediate blindness. Due to the occurrence of the choroidal neovascularization in the age-related macular degeneration, there are induced subretinal bleeding and subretinal exudation as well as retina detachment and fibrous proliferation, which can bring about a visual deterioration and occasionally blindness. Furthermore, it is known that when diabetes mellitus has progressed, a proliferative neovascularization is incurred in the retina, resulting in an onset of the proliferative diabetic retinitis and leading sometimes to blindness.

Hithertobefore, clinical therapeutic treatment of the neovascularization, which has occurred in the ocular fundus due to the age-related macular degeneration or the proliferative diabetic retinitis, has been done usually by making photo-coagulation of the neovascular vessels with irradiation of a laser light having a thermal action. It has been known that the photo-coagulation method made in the above prior art has a drawback that the thermal action of the laser light as employed can destroy even the surrounding normal tissues, whereas the neovascular vessels themselves can be occluded well by the thermal coagulation of them. However, if a selective occlusion of the neovascular vessels as formed in the ocular fundus could be made feasible by means of PDT with using a photosensitizer and a laser light irradiation, it can be expected that a satisfactory therapeutic method for selectively occluding the neovascular vessels in the ocular fundus would be developed and provided. In the past, therefore, a great number of research works have been carried out for further ophthalmological application of PDT.

DISCLOSURE OF THE INVENTION

An object of this invention is to provide such novel, photodynamic therapy methods which are able to selectively occlude the choroidal neovascular vessels and/or the retinal neovascular vessels without involving any damage or impairment in the retinal parenchymal tissue as well as in the retinal normal vascular vessels and the choroidal normal vascular vessels, while there is adopted here such PDT method comprising administrating mono-L-aspartyl chlorin e6 tetra-sodium salt as the photosensitizer and irradiating the laser light of 664 nm-wavelength, and which novel photodynamic therapy method can also be designed to be operated in the clinical practice with safety.

The present inventors have now carried out a series of experiments wherein mono-L-aspartyl chlorin e6 tetra-sodium salt (sometimes abbreviated as NPe6 hereinafter) is intravenously injected at varying doses to test animals of monkey having neovasculature lesions formed of such experimental choroidal neovascular vessels (abbreviated as CNV sometimes hereinafter) which have been produced according to a modification of the Ryan's method of irradiating an argon laser light onto the ocular fundi of monkeys [Arch. Ophthalmol., Vol. 100, pp. 1804–1809 (1982)], and wherein observations are made of time-dependent changes in the concentration of the administered NPe6 as uptaken and distributed in the normal retinal parenchymal tissue, also in the vascular walls of the retinal normal vascular vessels and in the vascular walls of the CNV present in said neovasculature lesions formed of the experimental CNV, after the intravenous administration of NPe6 was done, and wherein there are utilized, as a guiding sign, the time-dependent changes in the intensity of a red fluorescence which can be emitted from NPe6 as excited under irradiation of a laser light of 488 nm-wavelength.

From the results of these experiments made by the present inventors, it has now been found that the administered NPe6 can never permeate into the normal parenchymal tissue of the ocular retina. Additionally, it has also now been found that a significant quantity of the administered NPe6 can be uptaken and accumulated in the vascular walls of the retinal normal vascular vessels, before the administered NPe6 is uptaken in the vascular walls of CNV, and that a significant quantity of NPe6 can then permeate into the vascular walls of CNV, while the administered and accumulated NPe6 can subsequently continue to be cleared or eliminated from the retinal normal vascular walls at a higher clearance speed than from the vascular walls of CNV.

It is also now revealed that, during the course where NPe6 has once been uptaken and accumulated in the vascular walls of the retinal normal vascular vessels and is subsequently cleared or eliminated out of said vascular walls of the normal retinal vascular vessels, the NPe6 can commence to be uptaken into and accumulated in the vascular walls of the choroidal neovascular vessels (CNV), and that the concentration of NPe6 as uptaken and accumulated and remaining in the vascular walls of CNV can reach a peak of its concentration in about 20 minutes or thereabout after the time of the intravenous injection of NPe6. Furthermore, it is also now found that, in the course of the clearance or elimination of NPe6 from the vascular walls of the retinal normal vascular vessels, and also during a time period as lapsed after the observed complete clearance or elimination of NPe6 in the vascular walls of the retinal normal vascular vessels, NPe6 can continue to permeate and remain at a significant concentration of NPe6 preferentially in the vascular walls of CNV.

It is now further found that, after the administration of NPe6 to the monkeys under test, the time-dependent change in the concentration of NPe6 as uptaken and distributed in the vascular walls of the retinal normal vascular vessels can vary dependently on the doses of NPe6 administered, and that the time-dependent change in the concentration of NPe6 as uptaken and remaining in the vascular walls of CNV can also vary dependently on the doses of NPe6 administered. When the dose of the intravenously injected NPe6 is controlled within a range of 0.5 mg/kg to 10 mg/kg, it can also be found now that the concentration of the NPe6 remaining in the vascular walls of CNV can be retained at a remarkably higher value than that of the concentration of NPe6 remaining in the vascular walls of the retinal normal vascular vessels, as long as the determination of the NPe6 concentration is done at a certain chosen time point or time points after the intravenous injection of NPe6, though said time point(s) of determining the NPe6 concentration is or are altered with the doses of NPe6 administered; and further it is now found that the concentration of NPe6 remaining in the vascular walls of CNV can be retained at a significantly high value even after NPe6 had been completely or almost completely cleared or eliminated from the vascular walls of the retinal normal vascular vessels.

The present inventors have now found additionally that, when a laser light of 664 nm-wavelength is started to be irradiated to the CNV present in said neovasculature lesions, either at such a time point at which the concentration of NPe6 remaining in the vascular walls of the retinal normal vascular vessels has reached a value of the NPe6 concentration significantly lower than the value of the concentration of NPe6 remaining in the vascular walls of CNV, or at such a time point at which a significant concentration of NPe6 can be observed to remain still in the vascular walls of CNV even after NPe6 can be observed to have been cleared or eliminated completely from the retinal normal vascular vessels; and also when the above-mentioned irradiation of the laser light of 664 nm-wavelength to the CNV in the neovasculature lesions is effected at an ingeniously adjusted fluence of said laser light, it is feasible that the vascular endothelial cells of the CNV so treated can successfully be destroyed photochemically and the CNV can thus be occluded preferentially or selectively, without involving any adverse effect in the retinal parenchymal tissue, the retinal normal vascular vessels and the choroidal normal vascular vessels.

In contrast, it has now been found that, if the laser light of 664 nm-wavelength is started to be irradiated at an inappropriate time point after the intravenous injection of NPe6, and/or if the fluence of said laser light is adjusted to an insufficient value or to an excessively high value of the fluence of the laser light even with the irradiation of said laser light being started at an appropriate time point, it is impossible to achieve the selective occlusion of CNV as desired.

Thus, it has now been found that, for instance, if the irradiation of the laser light of 664 nm-wavelength is started toward the neovasculature lesions at such an inappropriate time point when NPe6 is still remaining at a significantly high concentration of NPe6 in the vascular walls of the retinal normal vascular vessels, there can be involved undesired damage and undesired occlusion also in the retinal normal vascular vessels and the choroidal normal vascular vessels which are adjacent to said neovasculature lesions as exposed to said laser light. Further, it is useless that the irradiation of the laser light of 664 nm-wavelength is started at such a time point when the concentration of NPe6 remaining in the vascular walls of the neovasculature lesions has decreased to an inappropriately lowered value.

The present inventors have now found that, in order to achieve the object of this invention for attaining the selective occlusion of CNV, it is necessary that the laser light of 664 nm-wavelength is started to be irradiated at such a chosen appropriate time point when the concentration of NPe6 distributed and remaining in the vascular walls of the retinal normal vascular vessels has either reached a value of the NPe6 concentration sufficiently lower than the value of the concentration of NPe6 remaining in the vascular walls of CNV, or has reached a value of zero or a value close to zero; and also it is necessary that the fluence of the laser light of 664 nm-wavelength to be irradiated is controlled to an appropriate value. It may be considered that the above-mentioned various findings as obtained by the present inventors from the above-mentioned PDT experiments with monkeys may commonly be applicable to the PDT technique which is to be carried out to achieve a selective occlusion of the ocular neovascular vessels of human beings, because it is known that the structure of the ocular fundus tissue in the monkey eye is very similar to the structure of the ocular fundus tissue in the human eye. This invention has been accomplished on the basis of the above various findings of the present inventors.

In a first aspect of the invention, therefore, there is provided a photodynamic therapy method for occluding selectively such choroidal neovascular vessels and/or retinal neovascular vessels as formed in a mammalian animal having an ocular fundus tissue comprising the retinal normal parenchymal tissue, the retinal normal vascular vessels and the choroidal normal vascular vessels lying under the retina, as well as choroidal neovascular vessels and/or retinal neovascular vessels, by developing actions of the photochemical reaction of an administered photosensitizer as excited with an irradiating laser light, but without involving a substantial damage or impairment in the retinal normal parenchymal tissue, the retinal normal vascular vessels and the choroidal normal vascular vessels, characterized in that the method comprises:

(a) administering intravenously mono-L-aspartyl chlorin e6 or a pharmaceutically acceptable salt thereof, particularly mono-L-aspartyl chlorin e6 tetra-sodium salt as the photosensitizer to the animal at a dose of 0.5 mg/kg to 10 mg/kg (as calculated on the weight basis of mono-L-aspartyl chlorin e6 tetra-sodium salt) at a vein of the animal;

(b) allowing that the mono-L-aspartyl chlorin e6 or a salt thereof, particularly mono-L-aspartyl chlorin e6 tetra-sodium salt administered as the photosensitizer, which is carried along by the blood streams circulating in the ocular retinal central artery and ciliary artery, is uptaken in the endothelial cell layers of the retinal normal vascular vessels and also in the endothelial cell layers of the choroidal normal vascular vessels as well as in the endothelial cell layers of the retinal neovascular vessels and/or the endothelial cell layers of the choroidal neovascular vessels, and allowing that the administered photosensitizer is then distributed and accumulated in and being eliminated or cleared from the vascular walls of said normal vascular vessels and said neovascular vessels;

(c) subsequently irradiating and scanning a laser light of 488 nm-wavelength at a sufficient fluence of said laser light, intermittently or continuously, through the surface of the ocular cornea, pupil, lens and vitreous fluid of the eye, to and on said ocular fundus tissue of the animal, so as to induce emission of a red fluorescence from the photoexcited mono-L-aspartyl chlorin e6 having distributed in the vascular walls of said normal vascular vessels and of said neovascular vessels in said ocular fundus tissue; and further observing intermittently or continuously the intensity of the red fluorescence which is emitted from the photosensitizer having been exposed to the laser light of 488 nm-wavelength and having distributed in the vascular walls of the retinal normal vascular vessels as well as in the vascular walls of the choroidal neovascular vessels and/or the vascular walls of the retinal neovascular vessels, with using a fluorescence ocular fundus angiography apparatus or a fluorescence microscope for funduscopy, for this observation;

(d) using said fluorescence ocular fundus angiography apparatus or fluorescence microscope for funduscopy during the irradiation of the 488 nm-wavelength laser light, to estimate such a time point at which, in the course of the elimination or clearance of the photosensitizer out of the vascular walls of the retinal normal vascular vessels and the choroidal normal vascular vessels, the intensity of the red fluorescence emitted from the photosensitizer present in the vascular walls of the retinal normal vascular vessels under observation can be observed to have decreased to a lowered value of about one-half-folds or less, particularly ⅓-folds or less of the intensity of the red fluorescence emitted from the photosensitizer remaining in the vascular walls of the neovascular vessels under observation; and thus to estimate such time point at which it can be revealed from the observation of the decrease in the intensity of the emitted red fluorescence by means of said fluorescence ocular fundus angiography apparatus or fluorescence microscope for funduscopy that the concentration of the photosensitizer present in the vascular walls of the retinal normal vascular vessels under observation has decreased to a lowered value of about one-half-folds or less, particularly ⅓-folds or less of the concentration of the photosensitizer remaining in the vascular walls of the neovascular vessels under observation;

(e) at the time point so estimated in the above step (d) or within a time of 1 to 10 minutes from the so estimated time point; starting to irradiate a laser light of 664 nm-wavelength in the form of a thin laser beam, via the cornea, pupil and vitreous fluid of the eye, exclusively to such targeted lesions comprising the neovasculature formed of said neovascular vessels in the ocular fundus, in such a way that said laser light of 664 nm-wavelength is irradiated at a fluence of said laser light necessary to excite the photosensitizer remaining in the vascular walls of the neovascular vessels; and (f) subsequently permitting that the lumens of the neovascular vessels contained in said lesions as irradiated with the laser light of 664 nm-wavelength are occluded by the developed actions of the photochemical reaction of the laser-excited photosensitizer remaining in the vascular walls of said neovascular vessels, whereby a selective occlusion of the choroidal neovascular vessels and/or the retinal neovascular vessels is achieved.

According to the first aspect method of this invention, the photosensitizer may usually be generally administered intravenously at a vein other than the ocular veins but may be administered also at an intraocular vein if a possible means is available therefor.

Mono-L-aspartyl chlorin e6 is a compound which may be produced by the method described in Example 19 of the specification of U.S. Pat. No. 4,675,338 described above. Mono-L-aspartyl chlorin e6 is a substance having the chemical structure represented by the formula (A):

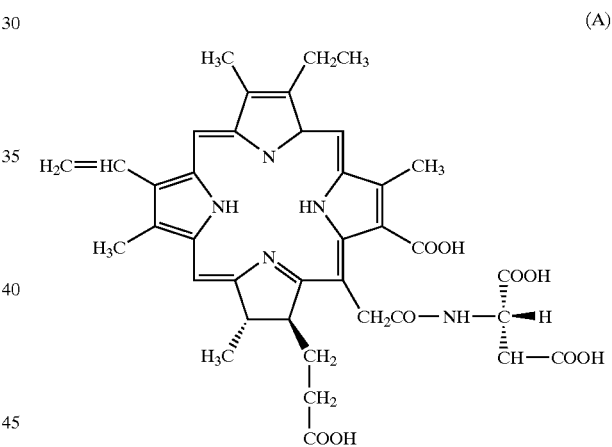

In this invention, the term "mammalian animal" means an animal, including humans. Generally, the mono-L-aspartyl chlorin e6 as used in this invention may be in the form of a salt thereof with a base. The salt with a base may include, for example, the salts with sodium, potassium, calcium, magnesium, ammonium, triethylammonium, trimethylammonium, morpholine and piperidine.

When acute toxicity of mono-L-aspartyl chlorin e6 was tested, it is also found that the $LD_{50}$ of mono-L-aspartyl chlorin e6 tetra-sodium salt in CD-1 (male) mice is 164 mg/kg. From phototoxicity test, it is also found that mono-L-aspartyl chlorin e6 tetra-sodium salt has got an approval as a safe compound which dose not involve any side-reaction of inducing erythema, edema and others.

For a laser source of irradiation of the laser light of 664 nm-wavelength which is to be used in the method of this invention, it is possible to use a semiconductors for continuous potent laser oscillation which is provided with optical filters; or excited dyes; or other laser delivery systems. The laser irradiation source may desirably be such one which is capable of oscillating a laser beam of a wavelength of 620 to 760 nm at an irradiance of 10 to 1500 mW/cm$^2$. Several of laser oscillators which are currently commercially available may satisfy the aforementioned criteria for the laser oscillation.

According to the method of the first aspect of this invention, the fluorescence, which is emitted from mono-L-aspartyl chlorin e6 as distributed and remaining in the vascular walls after the administration thereof, may be observed by using, for example, a scanning laser ophthalmoscope (abbreviated as SLO; manufactured by Rodenstock, Co.), with exciting the mono-L-aspartyl chlorin e6 under irradiation of an argon laser light of 488 nm-wavelength.

In the method of the first aspect of this invention, it is feasible that, in the step (e) of the method, the irradiation of the laser light of 664 nm-wavelength via the surface of cornea, pupil and vitreous fluid of the eye exclusively to the targeted lesions comprising the neovasculature formed of the neovascular vessels in the ocular fundus is started at such a time point when a time period of 10 to 70 minutes has lapsed after the time of the intravenous injection of mono-L-aspartyl chlorin e6 or a salt thereof, particularly mono-L-aspartyl chlorin e6 tetra-sodium salt; provided that said time point is also the time point when it can be estimated from the observation of the decreases in the intensity of the red fluorescence as emitted from the photosensitizer remaining in the vascular walls by excitation of said photosensitizer with the irradiation of the laser light of 488 nm-wavelength, with using the fluorescence ocular fundus angiography apparatus or the fluorescence microscope for funduscopy for the purpose of said observation, that the concentration of said photosensitizer present in the vascular walls of the retinal normal vascular vessels has decreased just to a lowered value of about one-half-folds or less of the concentration of the photosensitizer remaining in the vascular walls of the choroidal neovascular vessels and/or the vascular walls of the retinal neovascular vessels.

In the method of the first aspect of this invention, it is also feasible that, in the step (d) of the method, there is estimated such a time point when a time period of 20 to 70 minutes has lapsed after the time of the intravenous injection of mono-L-aspartyl chlorin e6 or a salt thereof, particularly mono-L-aspartyl chlorin e6 tetra-sodium salt; provided that said time point is also such time point when it can be revealed from the observation with the fluorescence ocular fundus angiography apparatus or fluorescence microscope for funduscopy during the irradiation of the 488 nm-wavelength laser light, that the intensity of the red fluorescence emitted from the said photosensitizer remaining in the vascular walls of the choroidal neovascular vessels and/or the retinal neovascular vessels has reached its peak value under the irradiation of the laser light of 488 nm-wavelength; and provided that said time point is further such time point when it is additionally observed by said fluorescence ocular fundus angiography apparatus or fluorescence microscope for funduscopy that the red fluorescence as emitted from the photosensitizer still remaining in the vascular walls of the retinal normal vascular vessels has disappeared completely during the irradiation of the laser light of 488 nm-wavelength made at a sufficiently high fluence of said laser light. And, it is then feasible that just at the time point so estimated in the above, the laser light of 664 nm-wavelength is started in the step (e) of the method to be irradiated through the surface of cornea, pupil and vitreous fluid of the eye exclusively to the targeted lesions comprising the neovasculature formed of the neovascular vessels in the ocular fundus.

In the method of the first aspect of this invention, it is preferred that the laser light of 664 nm-wavelength, which is irradiated to the targeted neovasculature lesions comprising the neovascular vessels in the ocular fundus, has an irradiance of 10 to 1500 mW/cm$^2$, preferably 0.5 to 0.8 W/cm$^2$ on the top retina face, as measured at the corneal surface by means of an optical power meter, and said laser light of 664 nm-wavelength is irradiated for a duration of 10 to 300 seconds and at a fluence of the laser light in a range of 7.0 J/cm$^2$ to 250 J/cm$^2$, preferably 7.5 J/cm$^2$ to 205 J/cm$^2$; provided that said fluence of the laser light is evaluated by multiplying the laser irradiance (in W/cm$^2$) by the duration of the laser irradiation (in seconds), whereupon the lower is the dose of mono-L-aspartyl chlorin e6, the fluence of the laser light to be irradiated may be controlled to be the higher, so as to achieve the selective occlusion of the neovascular vessels present in the targeted neovasculature lesions.

In the method of the first aspect of this invention, it is also possible that the laser light of 664 nm-wavelength is started in the step (e) of the method to be irradiated at such a time point when a time period of 20 to 70 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 0.5 mg/kg to 10.0 mg/kg [as calculated on the weight basis of mono-L-aspartyl chlorin e6 tetra-sodium salt, namely NPe6; though the same way of this calculation is applied hereinafter), and that the fluence of the laser light of 664 nm-wavelength to be irradiated is controlled within a range of 7 J/cm$^2$ to 205 J/cm$^2$. It is further possible that the laser light of 664 nm-wavelength is started in the step (e) of the method to be irradiated at such a time point when a time period of 20 to 30 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 0.5 mg/kg to 0.9 mg/kg (as calculated on the weight basis of NPe6), and that the fluence of the laser light of 664 nm-wavelength to be irradiated is controlled within a range of 175 J/cm$^2$ to 205 J/cm$^2$.

In the method of the first aspect of this invention, it is furthermore possible that the laser light of 664 nm-wavelength is started in the step (e) of the method to be irradiated at such a time point when a time period of 30 to 60 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 1 mg/kg to 1.9 mg/kg (as calculated on the weight basis of NPe6), and that the fluence of the laser light of 664 nm-wavelength to be irradiated is controlled within a range of 30 J/cm$^2$ to 175 J/cm$^2$, preferably 34 J/cm$^2$ to 171 J/cm$^2$.

In the first aspect method of this invention, it is further possible that the laser light of 664 nm-wavelength is started in the step (e) of the method to be irradiated at such a time point when a time period of 60 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 2 mg/kg to 9.5 mg/kg (as calculated on the weight basis of NPe6), and that the fluence of the laser light of 664 nm-wavelength to be irradiated is controlled within a range of 30 J/cm$^2$ to 45 J/cm$^2$.

In the first aspect method of this invention, besides, it is possible that the laser light of 664 nm-wavelength is started in the step (e) of the method to be irradiated at such a time point when a time period of 60 to 70 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 9.5 mg/kg to 10 mg/kg (as calculated on the weight basis of NPe6), and that the fluence of the laser light of 664 nm-wavelength to be irradiated is controlled within a range of 7 J/cm$^2$ to 9 J/cm$^2$, preferably 7.5 J/cm$^2$ to 8 J/cm$^2$.

In the method according to the first aspect of this invention, the mammalian animal to be treated may be a human having suffered from age-related macular degeneration with the choroidal neovascular vessels, or a human having suffered from proliferative diabetic retinitis with proliferative neovascular vessels in the retina.

In the first aspect method of this invention as described hereinbefore, the intensity of the red fluorescence emitted from mono-L-aspartyl chlorin e6, particularly NPe6 having distributed and remaining in the vascular walls of the retinal normal vascular vessels is observed, in comparison with the concurrently observed intensity of the red fluorescence emitted from mono-L-aspartyl chlorin e6 having distributed and remaining in the vascular walls of CNV in the neovasculature lesions, in such a manner that these observations are made under irradiation of an infrared light of 488 nm-wavelength and with using a fluorescence ocular fundus angiography apparatus or a similar means. Thereby, it can be detected that a difference exists normally between the concentration of mono-L-aspartyl chlorin e6 having distributed and remaining in the vascular walls of the retinal normal vascular vessels and the concentration of mono-L-aspartyl chlorin e6 having distributed and remaining in the vascular walls of CNV, whereby it can be estimated when is an appropriate time point at which the irradiation of the laser light beam of 664 nm-wavelength is to be started. However, in fact, the red fluorescence emitted from the mono-L-aspartyl chlorin e6 having distributed and remaining in the vascular walls of the normal vascular vessels, as well as the red fluorescence emitted from the mono-L-aspartyl chlorin e6 having distributed and remaining in the vascular walls of CNV are both emitted at a very low intensity even under the irradiation of the infrared light of 488 nm. Therefore, a considerable skillness is needed usually for the observing persons in order to estimate the time-dependent changes in the intensity of the red fluorescence of mono-L-aspartyl chlorin e6 present in the vascular walls. In particular, when mono-L-aspartyl chlorin e6 is given at a low dose of 0.5 mg/kg or 1 mg/kg, it is needed to use various measures such that the sensitivity of the fluorescence ocular fundus angiography apparatus is elevated to a maximum.

For these reasons, the present inventors have now further made another researches in order to find out and examine if it is possible to develop a further simpler process which can determine the concentrations of mono-L-aspartyl chlorin e6 having distributed and remaining in the vascular walls of the retinal normal vascular vessels and of the neovascular vessels, in place of the above-mentioned process comprising observing the red fluorescence which is emitted from the mono-L-aspartyl chlorin e6 having distributed and remaining in the vascular walls of the retinal normal vascular vessels and of the neovascular vessels in the ocular fundus. Upon making these another researches, the present inventors have paid their attention on an infrared fluorescent substance, indocyanine green (abbreviated as ICG) which is conventionally and frequently used in the prior art diagnosis method of making the infrared fluorescence fundus angiography of the neovascular vessels in the ocular fundus of a patient with age-related macular degeneration. ICG has the same biochemical properties as those of NPe6 in the following points, that is, (i) ICG is hydrophilic similarly to NPe6; (ii) ICG has a molecular weight almost equal to NPe6; and (iii) ICG has a high affinity to lipoprotein. These indicated biochemical properties (i) to (iii) for a medicinal compound are known to play significant roles in the pharmacodynamics of the medicinal compound when administered to patients. Additionally, it is known that ICG can emit a sufficiently stronger fluorescence than NPe6.

The present inventors have now carried out a series of further experiments with using test monkeys which have the experimental CNV in the retina, and which were used in the aforesaid experiments of making the intravenous administration of NPe6. In this series of further experiments, indocyanine green (ICG) is intravenously injected to the test monkeys at a dose of 0.5 mg/kg to 1 mg/kg, which dose is conventional in the routine method of making the fluorescence fundus angiography of the ocular fundus of human patients. Then, the present inventors have examined the time-dependent change in the intensity of infrared fluorescence of ICG as distributed and remaining in the vascular walls of the retinal normal vascular vessels in the monkeys, in comparison with the time-dependent change in the intensity of infrared fluorescence of ICG as distributed and remaining in the vascular walls of CNV in the neovasculature lesions in the ocular fundus of the test monkeys, according to the routine diagnosis method of making the infrared fluorescence fundus angiography of the ocular fundus of human patients.

The above-mentioned series of the further experiments has now been found to reveal that the manner or pattern of the time-dependent change in the intensity of the infrared fluorescence of ICG as distributed and remaining in the vascular walls of the retinal normal vascular vessels, as well as the manner or pattern of the time-dependent change in the intensity of the infrared fluorescence of ICG as distributed and remaining in the vascular walls of CNV in the neovasculature lesions in the ocular fundus of the test monkeys having received the intravenous injection of ICG at its dose of 0.5 mg/kg to 1 mg/kg, are, respectively, very much well analogous to the manner or pattern of the time-dependent change in the intensity of the red fluorescence of NPe6 as distributed and remaining in the vascular walls of the retinal normal vascular vessels, as well as the manner or pattern of the time-dependent change in the intensity of the red fluorescence of NPe6 as distributed and remaining in the vascular walls of CNV in the neovasculature lesions in the ocular fundus of the test monkeys having received the intravenous injection of NPe6 at its dose of 05 mg/kg to 1 mg/kg.

Accordingly, the present inventors have thus presumed that the patterns or manners of the time-dependent changes in the intensity of the infrared fluorescence of ICG as distributed and remaining in the vascular walls of the retinal normal vascular vessels and the patterns or manners of the time-dependent change in the intensity of the infrared fluorescence of ICG as distributed and remaining in the vascular walls of CNV in the ocular fundus of the monkeys having received the intravenous injection of ICG at a dose of 0.5 mg/kg to 1 mg/kg, are respectively able to predict and indicate the time-dependent changes in the concentrations of NPe6 as distributed and remaining in the vascular walls of the retinal normal vascular vessels and the time-dependent change in the concentration of NPe6 as distributed and remaining in the vascular walls of CNV in the ocular fundus of the test monkeys having received the intravenous injection of NPe6 at a dose of 0.5 mg/kg to 1 mg/kg.

Consequently, the present inventors have now devised a new process wherein ICG is, at first, intravenously injected at a dose of 0.5 mg/kg to 1 mg/kg to the test monkeys prior to an intravenous injection of NPe6, and wherein the known diagnosis method of making the infrared fluorescence fundus angiography of the ocular fundus is utilized in order to estimate either such a time point at which the intensity of the infrared fluorescence emitted from the ICG having distributed, accumulated and remaining in the vascular walls of the retinal normal vascular vessels is decreased to a significantly lower value than that of the intensity of the infrared fluorescence emitted from the ICG having distributed, accumulated and remaining in the vascular walls of CNV in the ocular fundus, or such a time point at which the infrared fluorescence of ICG has been eliminated from the vascular walls of the retinal normal vascular vessels, whereas the infrared fluorescence of ICG having accumulated and remaining in the vascular walls of CNV in the ocular fundus is still observable and appreciable at a significant intensity, and wherein calculation is then made of a value of such a time-gap as extended between the time point estimated in the above and the first time of the intravenous injection of ICG.

The present inventors have thus now presumed that it is made possible by the so devised process as above to estimate and decide such an appropriate time-point at which the irradiation of a laser light of 664 nm-wavelength is to be started for the photo-excitation of NPe6 as injected, and namely at which the concentration of the NPe6 having distributed and remaining in the vascular walls of the retinal normal vascular vessels of the test monkeys having received the intravenous injection of NPe6 has decreased to a significantly lower value than that of the concentration of the NPe6 having accumulated and remaining in the vascular walls of CNV in the ocular fundus of the monkeys. On the basis of these findings of the present inventors, a second aspect of this invention as described hereinafter has now been accomplished.

In a second aspect of this invention, therefore, there is provided a photodynamic therapy method for occluding selectively such choroidal neovascular vessels and/or retinal neovascular vessels as formed in a mammalian animal having an ocular fundus tissue comprising the retinal normal parenchymal tissue, the retinal normal vascular vessels and the choroidal normal vascular vessels lying under the retina, as well as choroidal neovascular vessels and/or retinal neovascular vessels, by developing actions of the photochemical reaction of an administered photosensitizer as excited with an irradiating laser light, but without involving a substantial damage or impairment in the retinal normal parenchymal tissue, the retinal normal vascular vessels and the choroidal normal vascular vessels, characterized in that the method comprises:

(a) administering firstly indocyanine green intravenously to the animal at a dose of 0.5 mg/kg to 1 mg/kg at a vein of said animal;

(b) allowing that the indocyanine green, which is carried along by the blood streams circulating in the ocular retinal central artery and ciliary artery, is uptaken in the endothelial cell layers of the retinal normal vascular vessels and also in the endothelial cell layers of the choroidal normal vascular vessels as well as in the endothelial cell layers of the choroidal neovascular vessels and/or the endothelial cell layers of the retinal neovascular vessels, and allowing that the indocyanine green is then distributed and accumulated in and being eliminated or cleared from the vascular walls of said normal vascular vessels and said neovascular vessels;

(c) subsequently irradiating and scanning a laser light containing a light of a 790 nm-wavelength at a sufficient fluence of said laser light, intermittently or continuously, through the surface of ocular cornea, pupil, lens and vitreous fluid of the eye, to and on the ocular fundus tissue of the animal, so as to induce emission of an infrared fluorescence from the photo-excited indocyanine green having distributed in the vascular walls of said normal vascular vessels and said neovascular vessels in said ocular fundus tissue; and further observing intermittently or continuously the intensity of the infrared fluorescence which is emitted from the indocyanine green having been exposed to the laser light of 790 nm-wavelength and having distributed in the vascular walls of the retinal normal vascular vessels as well as in the vascular walls of the choroidal neovascular vessels and/or the vascular walls of the retinal neovascular vessels, with using a fluorescence ocular fundus angiography apparatus or a fluorescence microscope for funduscopy, for this observation;

(d) using said fluorescence ocular fundus angiography apparatus or fluorescence microscope for funduscopy during the irradiation of the 790 nm-laser light, to estimate such a time point at which, in the course of the elimination or clearance of indocyanine green out of the vascular walls of the retinal normal vascular vessels and the choroidal normal vascular vessels, the intensity of the infrared fluorescence emitted from the indocyanine green present in the vascular walls of the retinal normal vascular vessels under observation can be observed to have decreased to a lowered value of about one-half-folds or less, particularly ⅓-folds or less of the intensity of the infrared fluorescence emitted from the indocyanine green remaining in the vascular walls of the neovascular vessels under observation; and thus to estimate such time point at which it can be revealed from the observation of the decreases in the intensity of the infrared fluorescence emitted from indocyanine green by means of said fluorescence ocular fundus angiography apparatus or fluorescence microscope for funduscopy that the concentration of the indocyanine green present in the vascular walls of the retinal normal vascular vessels under observation has decreased to a lowered value of about one-half-folds or less, particularly ⅓-folds or less of the concentration of the indocyanine green remaining in the vascular walls of the neovascular vessels under observation;

(e) calculating in a "minute" or "second" unit, such a time-gap as extended between the time of the first intravenous injection of indocyanine green and the aforesaid time point as estimated in the above step (d), namely the time point as estimated in the above step (d) at which the intensity of the infrared fluorescence emitted from the indocyanine green present in the vascular walls of the retinal normal vascular vessels has decreased to the lowered value of about one-half-folds or less of the intensity of the indocyanine green remaining in the vascular walls of the neovascular vessels as prescribed in the above step (d);

(f) allowing a time to pass by the time when it can observed that the infrared fluorescence of the indocyanine green remaining in the vascular walls of the choroidal neovascular vessels and/or retinal neovascular vessels has disappeared completely;

(g) administering then mono-L-aspartyl chlorin e6 or a pharmaceutically acceptable salt thereof, particularly mono-L-aspartyl chlorin e6 tetra-sodium salt to the animal intravenously at a dose in a range of 0.5 mg/kg to 10 mg/kg, preferably 0.5 mg/kg to 1 mg/kg (as calculated on the weight basis of NPe6) as the photosensitizer at a vein of said animal, after the time when the infrared fluorescence of the indocyanine green remaining in the vascular walls of said neovascular vessels under the irradiation of the 790 nm-wavelength laser light can be observed to have disappeared completely as described in the above step (f);

(h) allowing that mono-L-aspartyl chlorin e6 or a salt thereof, particularly mono-L-aspartyl chlorin e6 tetra-sodium salt as the photosensitizer, which is carried along by the blood streams circulating in the ocular retinal central artery and ciliary artery, is uptaken in the endothelial cell layers of the retinal normal vascular vessels and also in the endothelial cell layers of the choroidal normal vascular vessels as well as in the endothelial cell layers of the choroidal neovascular vessels and/or the endothelial cell layers of the retinal neovascular vessels, and allowing that the administered chlorin e6 compound is then distributed and accumulated in and being eliminated or cleared from the vascular walls of said normal vascular vessels and of said neovascular vessels;

(i) permitting the administered photosensitizer, mono-L-aspartyl chlorin e6 compound, to be accumulated and remain in the vascular walls of the choroidal neovascular vessels and/or the retinal neovascular vessels, while the chlorin e6 compound is concurrently eliminated or cleared out of the vascular walls of the normal vascular vessels of the retina and choroid;

(j) at such time point when a time duration, which has a time length equal to that of the said time-gap (in the "minute" or "second" unit) as calculated in the above step (e), has just passed after the time of the intravenous injection of the mono-L-aspartyl chlorin e6 substance; starting to irradiate a laser light of 664 nm-wavelength in the form of a thin laser beam, via the surface of cornea, pupil and vitreous fluid of the eye, exclusively to such targeted lesions comprising the neovasculature formed of said neovascular vessels in the ocular fundus, in such a way that said laser light of 664 nm-wavelength is irradiated at a fluence of said laser light necessary to excite the photosensitizer remaining in the vascular walls of the neovascular vessels; and (k) subsequently permitting that the lumens of the neovascular vessels contained in said lesions as irradiated with the laser light of 664 nm-wavelength are occluded by the developed actions of the photochemical reaction of the laser-excited photosensitizer remaining in the vascular walls of said neovascular vessels, whereby a selective occlusion of the choroidal neovascular vessels and/or the retinal neovascular vessels is achieved.

In the method of the second aspect of this invention, it is possible that, in the step (j) of the method, the irradiation of the laser light of 664 nm-wavelength via the surface of cornea, pupil and vitreous fluid of the eye exclusively to the targeted lesions comprising the neovasculatures formed of the neovascular vessels in the ocular fundus is started at such a time point when a time period of 10 to 70 minutes, preferably 20 to 70 minutes has lapsed after the time of the intravenous administration of mono-L-aspartyl chlorin e6 or a salt thereof, particularly mono-L-aspartyl chlorin e6 tetra-sodium salt; provided that said time point is the such time point when there has just passed a time duration which has a time length equal to that of the said time-gap as calculated in the step (e) of the method according to the second aspect of this invention.

In the method of the second aspect of this invention, it is preferred that the laser light of 664 nm-wavelength, which is irradiated to the targeted lesions comprising the neovascular vessels in the ocular fundus, has an irradiance of 10 to 1500 mW/cm$^2$, preferably 0.5 to 0.8 W/cm$^2$ on the top retina face, as measured at the corneal surface by means of an optical power meter, and that the laser light of 664 nm-wavelength is irradiated for a duration of 10 to 300 second, and at a fluence of the laser light in a range of 7.0 J/cm$^2$ to 250 J/cm$^2$, preferably 7.5 J/cm$^2$ to 205 J/cm$^2$; provided that said fluence of the laser light is evaluated by multiplying the laser irradiance (in W/cm$^2$) by the duration of the laser irradiation (in seconds), whereupon the lower is the dose of mono-L-aspartyl chlorin e6, the fluence of the laser light of 664 nm-wavelength to be irradiated is controlled to be the higher, so as to achieve the selective occlusion of the neovascular vessels present in the target lesions.

Besides, in the method of the second aspect of this invention, it is possible that the irradiation of the laser light of 664 nm-wavelength is started in the step (j) of the method at such a time point when a time period of 20 to 70 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 0.5 mg/kg to 10.0 mg/kg (as calculated on the weight basis of NPe6), whereupon the fluence of the laser light of 664 nm-wavelength to be irradiated is controlled within a range of 7 J/cm$^2$ to 205 J/cm$^2$.

In the second aspect method, it is also possible that the irradiation of the laser light of 664 nm-wavelength is started in the step (j) of the method at such a time point when a time period of 20 to 30 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 0.5 mg/kg to 0.9 mg/kg (as calculated on the weight basis of NPe6), whereupon the fluence of the laser light of 664 nm-wavelength to be irradiated is controlled within a range of 175 J/cm$^2$ to 205 J/cm$^2$.

In the method of the second aspect of this invention, it is furthermore possible that the irradiation of the laser light of 664 nm-wavelength is started in the step (j) of the method at such a time point when a time period of 30 to 60 minutes has lapsed after the intravenous administration of mono-L-aspartyl chlorin e6 or a salt thereof, particularly mono-L-aspartyl chlorin e6 tetra-sodium salt, as long as the chlorin e6 compound is given at a dose of 1 mg/kg to 1.9 mg/kg (as calculated on the weight basis of NPe6), whereupon the fluence of the laser light of 664 nm-wavelength to be irradiated is controlled within a range of 30 J/cm$^2$ to 175 J/cm$^2$, preferably 34 J/cm$^2$ to 171 J/cm$^2$.

In the second aspect method of this invention, it is further possible that the irradiation of the laser light of 664 nm-wavelength is started in the step (j) of the method at such a time point when a time period of 60 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 2 mg/kg to 9.5 mg/kg (as calculated on the weight basis of NPe6), whereupon the fluence of the laser light of 664 nm-wavelength to be irradiated is controlled within a range of 30 J/cm$^2$ to 45 J/cm$^2$.

In the method of the second aspect of this invention, it is moreover possible that the irradiation of the laser light of 664 nm-wavelength is started in the step (j) of the method at such a time point when a time period of 60 to 70 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 9.5 mg/kg to 10 mg/kg (calculated on the weight basis of NPe6), whereupon the fluence of the laser light of 664 nm-wavelength to be irradiated is controlled within a range of 7 J/cm$^2$ to 9 J/cm$^2$, preferably 7.5 J/cm$^2$ to 8 J/cm$^2$.

Also in the method of the second aspect of this invention, the mammalian animal to be treated is a human having suffered from age-related macular degeneration with the choroidal neovascular vessels, or a human having suffered from proliferative diabetic retinitis with proliferative neovascular vessels.

As described hereinbefore in respect of the method of the second aspect of this invention, it has been revealed that, as long as ICG has been intravenously injected at a dose of 0.5 mg/kg to 1 mg/kg to the test monkeys having the experimental CNV in their ocular fundus, the pattern of the time-dependent change in the intensity of the infrared fluorescence emitted from the ICG having been uptaken, distributed and remaining in the vascular walls of the retinal normal vascular vessels, as well as the pattern of the time-dependent change in the intensity of the infrared fluorescence emitted from the ICG having been uptaken, distributed and remaining in the vascular walls of CNV in the ocular fundus of the monkeys under test are, respectively, able to predict and indicate the pattern of the time-dependent change in the concentration of the NPe6 having been uptaken, distributed and remaining in the vascular walls of the retinal normal vascular vessels, as well as the pattern of the time-dependent change in the concentration of the NPe6 having been uptaken, distributed and remaining in the vascular walls of CNV in the ocular fundus of the test monkeys in which NPe6 has been injected intravenously at dose of 0.5 mg/kg to 1 mg/kg.

Accordingly, the present inventors conclusively consider that, when ICG is intravenously injected at a dose of 0.5 mg/kg to 1 mg/kg to the test monkeys having the experimental CNV in their ocular fundus and then NPe6 is intravenously injected to said monkeys at a dose of 0.5 mg/kg to 10 mg/kg, or desirably at a dose of 0.5 mg/kg to 1 mg/kg as same as the dose of the intravenously injected ICG, either at the same time as the time of the intravenous injection of ICG, or immediately before or immediately after the intravenous injection of ICG, it occurs that both of ICG and NPe6 can concurrently be uptaken into and distributed in the vascular walls of the retinal normal vascular vessels and also in the vascular walls of the CNV in the ocular fundus of the monkeys. The present inventors also consider conclusively that the ICG and NPe6, which have been intravenously injected at the same time or at a substantially same time, are able to bring about the time-dependent change in the concentration of ICG and also the time-dependent change in the concentration of NPe6 within both of the vascular walls of the retinal normal vascular vessels and the vascular walls of the CNV in the ocular fundus of the monkeys, so that the time-dependent change in the concentration of NPe6 can take place concurrently in the same pattern or manner as the time-dependent change in the concentration of ICG in said vascular walls of the retinal normal vascular vessels and of the CNV.

Consequently, the present inventors have now attained such a concept that, when ICG is intravenously injected at a dose of 0.5 mg/kg to 1 mg/kg, and then NPe6 is intravenously injected at such a dose of NPe6 as same as the dose of the intravenously injected ICG and either at the same time as the time of the intravenous injection of ICG or at a substantially same time as the time of the intravenous injection of ICG, it are practically feasible to conduct an indirect observation of the time-dependent change in the concentration of the NPe6 having distributed and remaining in the vascular walls of the retinal normal vascular vessels, and also to conduct an indirect observation of the time-dependent change in the concentration of the NPe6 having distributed and remaining in the vascular walls of the CNV in the ocular fundus, by carrying out such known diagnosis method of the infrared fluorescence fundus angiography for the ocular fundus by which direct observation can be made of the time-dependent change in the intensity of the infrared fluorescence of the ICG having distributed and remaining in the vascular walls of the retinal normal vascular vessels, and by which also direct observation can be made of the time-dependent change in the intensity of the infrared fluorescence of the ICG having distributed and remaining in the vascular walls of the CNV in the ocular fundus. Further, the present inventors have now concluded that the above-mentioned method of conducting the indirect observation of the time-dependent changes in the intensity of ICG remaining in the vascular walls of the retinal normal vascular vessels, as well as the indirect observation of the time-dependent change in the intensity of ICG remaining in the vascular walls of the CNV in the ocular fundus, is able to estimate and determine the appropriate time point at which there may be started the required irradiation of the laser light of 664 nm-wavelength to the neovasculature lesions formed of CNV in the ocular fundus. On the basis of these findings, a third aspect of this invention has been accomplished.

In the third aspect of this invention, therefore, there is provided a photodynamic therapy method for occluding selectively such choroidal neovascular vessels and/or retinal neovascular vessels as formed in a mammalian animal having an ocular fundus tissue comprising the retinal normal parenchymal tissue, the retinal normal vascular vessels and the choroidal normal vascular vessels lying under the retina, as well as choroidal neovascular vessels and/or retinal neovascular vessels, by developing actions of the photochemical reaction of an administered photosensitizer as excited with an irradiating laser light, but without involving any substantial damage or impairment in the retinal normal parenchymal tissue, the retinal normal vascular vessels and the choroidal normal vascular vessels, characterized in that the method comprises:

(a) administering intravenously mono-L-aspartyl chlorin e6 or a pharmaceutically acceptable salt thereof, particularly mono-L-aspartyl chlorin e6 tetra-sodium salt as the photosensitizer to the animal at a dose of 0.5 mg/kg to 10 mg/kg (as calculated on the weight basis of NPe6) at a vein of the animal; and also injecting intravenously indocyanine green to the animal at a dose in a range of 0.5 mg/kg to 1 mg/kg, at the same time as or immediately before or after said intravenous administration of the mono-L-aspartyl chlorin e6 compound;

(b) allowing that mono-L-aspartyl chlorin e6 or a salt thereof, particularly mono-L-aspartyl chlorin e6 tetra-sodium salt, administered as the photosensitizer and also indocyanine green, which are carried along by the blood streams circulating in the ocular retinal central artery and ciliary artery, are uptaken in the endothelial cell layers of the retinal normal vascular vessels and also in the endothelial cell layers of the choroidal normal vascular vessels as well as in the endothelial cell layers of the retinal neovascular vessels and/or the endothelial cell layers of the choroidal neovascular vessels, and allowing that the chlorin e6 compound and indocyanine green as administered are then distributed and accumulated in and being eliminated or clearedfrom the vascular walls of said normal vascular vessels and said neovascular vessels;

(c) subsequently irradiating and scanning a laser light containing a light of 790 nm-wavelength, intermittently or continuously, through the surface of ocular cornea, pupil, lens and vitreous fluid of the eye, to and on the ocular fundus tissue of the animal, so as to induce emission of an infrared fluorescence from the photo-excited indocyanine green selectively, in the co-presences of the mono-L-aspartyl chlorin e6 and indocyanine green having distributed and remaining in the vascular walls of said vascular vessels of the ocular fundus tissue; and further observing intermittently or continuously, the intensity of the infrared fluorescence as emitted from the indocyanine green having distributed and remaining in the vascular walls of the retinal normal vascular vessels, as well as in the vascular walls of the choroidal neovascular vessels and/or the vascular walls of the retinal neovascular vessels, with using a fluorescence ocular fundus angiography apparatus or fluorescence microscope for funduscopy for this observation;

(d) using said fluorescence ocular fundus angiography apparatus or fluorescence microscope for funduscopy during the irradiation of 790 nm-wavelength, to estimate such a time point at which, in the course of the eliminations or clearances of the mono-L-aspartyl chlorin e6 substance and indocyanine green from the vascular walls of the retinal normal vascular vessels and the choroidal normal vascular vessels, the intensity of the infrared fluorescence emitted from the indocyanine green present in the vascular walls of the retinal normal vascular vessels under observation can be observed to have decreased to a lowered value of about one-half-folds or less, particularly ⅓-folds or less of the intensity of the infrared fluorescence emitted from the indocyanine green remaining in the vascular walls of the neovascular vessels under observation; and thus to estimate the such time point at which it can be revealed from the observation of the decreases in the intensity of the infrared fluorescence emitted from the indocyanine green by means of the fluorescence ocular fundus angiography apparatus or fluorescence microscope for funduscopy that the concentration of the photosensitive mono-L-aspartyl chlorin e6 compound present in the vascular walls of the retinal normal vascular vessels under observation has decreased to a lowered value of about one-half-folds or less, particularly ⅓-folds or less of the concentration of the photosensitive mono-L-aspartyl chlorin e6 compound remaining in the vascular walls of the neovascular vessels under observation;

(e) at the time point so estimated in the above step (d) or within a time of 1–10 minutes from the so estimated time point; starting to irradiate a laser light of 664 nm-wavelength in the form of a thin laser beam, via the surface of cornea, pupil and vitreous fluid of the eye, exclusively to such targeted lesions comprising the neovasculature formed of said neovascular vessels in the ocular fundus, in such a way that said laser light of 664 nm-wavelength is irradiated at a fluence of said laser light necessary to excite said photosensitive chlorin e6 compound remaining in the vascular walls of the neovascular vessels; and (f) subsequently permitting that the lumens of the neovascular vessels contained in said lesions as irradiated with the laser light of 664 nm-wavelength are occluded by the developed actions of the photochemical reaction of the laser-excited mono-L-aspartyl chlorin e6 compound remaining in the vascular walls of said neovascular vessels, whereby a selective occlusion of the choroidal neovascular vessels and/or the retinal neovascular vessels is achieved.

In the method of the third aspect of this invention, it is possible that, in the step (e) of this method, the irradiation of the laser light of 664 nm-wavelength via the surface of cornea, pupil and vitreous fluid of the eye exclusively to the targeted lesions comprising the neovasculature formed of the neovascular vessels in the ocular fundus is started at such a time point when a time period of 10 to 70 minutes has lapsed after the time of the intravenous administration of mono-L-aspartyl chlorin e6 or a salt thereof, particularly mono-L-aspartyl chlorin e6 tetra-sodium salt; provided that said time point is also the such time point when it can be revealed and estimated from the observation of the decreases in the intensity of the infrared fluorescence as emitted from the indocyanine green having distributed and remaining in the vascular walls by excitation of the indocyanine green under the irradiation of the laser light containing the laser light of 790 nm-wavelength, with using the fluorescence ocular fundus angiography apparatus or the fluorescence microscope for funduscopy, that the concentration of the photosensitive mono-L-aspartyl chlorin e6 compound present in the vascular walls of the retinal normal vascular vessels has decreased to a lowered value of about one-half-folds or less of the concentration of the photosensitive mono-L-aspartyl chlorin e6 compound remaining in the vascular walls of the choroidal neovascular vessels and/or the retinal neovascular vessels.

In the method of the third aspect of this invention, it is also possible that, in the step (d) of this method, there is estimated such a time point when a time period of 20 to 70 minutes has lapsed after the time of the intravenous injection of mono-L-aspartyl chlorin e6 or a salt thereof, particularly mono-L-aspartyl chlorin e6 tetra-sodium salt; provided that said time point is also such time point when it can be revealed from the observation with the fluorescence ocular fundus angiography apparatus or fluorescence microscope for funduscopy that the intensity of the infrared fluorescence emitted from the indocyanine green remaining in the vascular walls of the choroidal neovascular vessels and/or the retinal neovascular vessels has reached its peak value under the irradiation of the laser light containing the laser light of 790 nm-wavelength; and provided that said time point is further the such time point when it is also observed by said fluorescence ocular fundus angiography apparatus or fluorescence microscope for funduscopy that the infrared fluorescence as emitted from the indocyanine green still remaining in the vascular walls of the retinal normal vascular vessels has disappeared completely even under the irradiation of said laser light containing the light of 790 nm-wavelength; and it is also possible that in this method, subsequently just at the time point so estimated in the above, the laser light of 664 nm-wavelength is then started in the step (e) of this method to be irradiated through the surface of cornea, pupil and vitreous fluid of the eye exclusively to such targeted lesions comprising the neovasculature formed of the neovascular vessels in the ocular fundus.

In the method of the third aspect of this invention, it is preferred that the laser light of 664 nm-wavelength which is irradiated to the targeted lesions comprising the neovascular vessels in the ocular fundus, has an irradiance of 10 to 1500 mW/cm$^2$, preferably 0.5 to 0.8 W/cm$^2$ on the top retina face, as measured at the corneal surface by means of an optical power meter, and said laser light of 664 nm-wavelength is irradiated for a duration of 10 to 300 seconds and at a fluence of the laser light in a range of 7.0 J/cm$^2$ to 250 J/cm$^2$, preferably 7.5 J/cm$^2$ to 205 J/cm$^2$, provided that said fluence of the laser light is evaluated by multiplying the laser irradiance (in W/cm$^2$) by the duration of the laser irradiation (in seconds), whereupon the lower is then the dose of mono-L-aspartyl chlorin e6, the fluence of the laser light of 664 nm to be irradiated is controlled to be the higher, so as to achieve the selective occlusion of the neovascular vessels present in the targeted lesions.

In the method of the third aspect of this invention, it is possible that the laser light of 664 nm-wavelength is started in the step (e) of this method to be irradiated at such a time point when a time period of 20 to 70 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 0.5 mg/kg to 10.0 mg/kg (as calculated on the weight basis of NPe6), and that the fluence of the laser light of 664 nm-wavelength to be irradiated is controlled within a range of 7 J/cm$^2$ to 205 J/cm$^2$.

In this method, it is also possible that the laser light of 664 nm-wavelength is started in the step (e) of this method to be irradiated at such a time point when a time period of 20 to 30 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 0.5 mg/kg to 0.9 mg/kg (as calculated on the weight basis of NPe6), and that the fluence of the laser light of 664 nm-wavelength to be irradiated is controlled within a range of 175 J/cm$^2$ to 205 J/cm$^2$.

In the method of the third aspect of this invention, it is furthermore possible that the laser light of 664 nm-wavelength is started in the step (e) of this method to be irradiated at such a time point when a time period of 30 to 60 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 1 mg/kg to 1.9 mg/kg (as calculated on the weight basis of NPe6), and that the fluence of the laser light of 664 nm-wavelength to be irradiated is controlled within a range of 30 J/cm$^2$ to 175 J/cm$^2$, preferably 34 J/cm$^2$ to 171 J/cm$^2$.

In this method, it is moreover possible that the laser light of 664 nm-wavelength is started in the step (e) of this method to be irradiated at such a time point when a time period of 60 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 2 mg/kg to 9.5 mg/kg (as calculated on the weight basis of NPe6), and that the fluence of the laser light of 664 nm-wavelength to be irradiated is controlled within a range of 30 J/cm$^2$ to 45 J/cm$^2$.

In the method of the third aspect of this invention, it is also feasible that the laser light of 664 nm-wavelength is started in the step (e) of this method to be irradiated at such a time point when a time period of 60 to 70 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 9.5 mg/kg to 10 mg/kg (as calculated on the weight basis of NPe6), and that the fluence of the laser light of 664 nm-wavelength to be irradiated is controlled within a range of 7 J/cm$^2$ to 9 J/cm$^2$, preferably 7.5 J/cm$^2$ to 8 J/cm$^2$.

In the method of the third aspect of this invention, the mammalian animal to be treated may be a human having suffered from age-related macular degeneration with the choroidal neovascular vessels, or a human having suffered from proliferative diabetic retinitis with proliferative neovascular vessels in the retina.

In the methods of this invention as described hereinbefore, it is preferred to use mono-L-aspartyl chlorin e6 tetra-sodium salt as the photosensitizer. Mono-L-aspartyl chlorin e6 tetra-sodium salt (abbreviated as NPe6) may be intravenously administered in the form of its aqueous solution. In the aqueous solution of NPe6 for the intravenous injections, generally, the solvent usable for the injections may be, for example, water, aqueous ethanol or an aqueous polyol (for example, glycerol, propylene glycol, a liquid polyethylene glycol, and others), or a desirable mixture of two or more of these solvents. The fluidity of the injectable aqueous solution may be adjusted by incorporation of a viscosity adjustor such as lecithin. In many cases, an isotonic agent such as sugar or sodium chloride may preferably be incorporated therein.

In a fourth aspect of this invention, there is provided as a novel product an intravenously administrable pharmaceutical composition for use in a diagnosis or a selective occlusion of choroidal neovascular vessels and/or retinal neovascular vessels in the ocular fundus of eye according to a photodynamic therapy method, characterized in that said pharmaceutical composition is in the form of a single dosage unit for the intravenous injection, and that the composition contains mono-L-aspartyl chlorin e6 tetra-sodium salt in a proportion thereof corresponding to a dose of 0.5 mg/kg to 10 mg/kg, preferably a dose of 0.5 mg/kg to 1 mg/kg of mono-L-aspartyl chlorin e6 tetra-sodium salt as an effective component, and that the composition further contains indocyanine green in a proportion thereof corresponding to a dose of 0.5 mg/kg to 1 mg/kg of indocyanine green as an indicator capable of detecting the time-dependent decrease of the concentration of the administered mono-L-aspartyl chlorin e6 tetra-sodium salt having accumulated and remaining in the vascular walls of the ocular, choroidal neovascular vessels and/or retinal neovascular vessels after the intravenous administration of said composition was done, and that the mono-L-aspartyl chlorin e6 tetra-sodium salt and indocyanine green contained in the intravenously administered single dosage unit of said composition are dissolved in an aqueous carrier for the intravenous injection.

The pharmaceutical composition according to the fourth aspect of this invention may suitably be used in the above-mentioned method of the third aspect of this invention. In said pharmaceutical composition, it is preferred that the weight ratio of mono-L-aspartyl chlorin e6 tetra-sodium salt to indocyanine green as contained in the single dosage unit of the composition is in a range of 1:2 to 1:0.05, or more desirably in a range of 2:1 to 1:2, or is at a weight ratio which is near to the ratio of 2:1 to 1:2.

A further aspect of this invention includes a use of mono-L-aspartyl chlorin e6 tetra-sodium salt in the manufacture of an intravenously administrable pharmaceutical composition for use in a diagnosis or a selective occlusion of ocular, choroidal neovascular vessels and/or retinal neovascular vessels of eye according to a photodynamic therapy method, wherein said pharmaceutical composition is in the form of a single dosage unit for the intravenous injection, and wherein the composition contains mono-L-aspartyl chlorin e6 tetra-sodium salt in a proportion thereof corresponding to a dose of 0.5 mg/kg to 10 mg/kg, preferably a dose of 0.5 mg/kg to 1 mg/kg of mono-L-aspartyl chlorin e6 tetra-sodium salt as an effective component, and wherein the composition further contains indocyanine green in a proportion thereof corresponding to a dose of 0.5 mg/kg to 1 mg/kg of indocyanine green as an indicator capable of detecting the time-dependent decrease of the concentration of the administered mono-L-aspartyl chlorin e6 tetra-sodium salt having accumulated and remaining in the vascular walls of the ocular, choroidal neovascular vessels and/or retinal neovascular vessels after the intravenous administration of said composition was done.

BEST MODE FOR CARRYING OUT THE INVENTION

This invention is now illustrated in detail with reference to the following Test Examples and illustrative Examples, but the invention is not limited to these Examples.

TEST EXAMPLE 1

Referential Example 1

In this Example, experiments were conducted to examine that, when the intravenous administration of mono-L-aspartyl chlorin e6 tetra-sodium salt had been done to monkeys having the experimentally produced choroidal neovaucular vessels (CNV) in the ocular fundus of the monkeys, the concentration of the mono-L-aspartyl chlorin e6 tetra-sodium salt having been uptaken, distributed and remaining in the vascular walls of the retinal normal vascular vessels of the monkeys, as well as the concentration of the mono-L-aspartyl chlorin e6 tetra-sodium salt having been uptaken, distributed and remaining in the vascular walls of the choroidal neovascular vessels (CNV) of the monkeys were time-dependently changing in manners or patterns different from each other.

The time-dependent changes in the concentrations of the mono-L-aspartyl chlorin e6 tetra-sodium salt (NPe6) having distributed and remaining in the vascular walls of the retinal normal vascular vessels and also in the vascular walls of the choroidal neovascular vessels (CNV) were observed by a fluorescence fundus angiography process, wherein the changing intensities of the red fluorescence as emitted from NPe6 present in said vascular walls were recorded by photography under irradiation of the laser light beam of 488 nm by means of as fluorescence fundus camera apparatus, and wherein the resulting photographed images of different gradations were examined by visual observation.

The detailed procedures of the above experiments are as follows. Thus, a beam of a laser light of 647 nm wavelenght as emitted from a krypton laser generator [Coherent Medical Laser generator, manufactured by Novua Omni Co.; having an output of 500 to 900 mW] was irradiated as a laser-irradiating spot of a diameter of 50 $\mu$m onto the ocular fundi of 8 mature monkeys of the genus *Macaca* (of body weights of 3.5 kg to 6.0 kg) for 0.1 seconds, according to a modification of the Ryan's method [Arch. Ophthalmol., vol 100; pp. 1804–1809 (1982)]. It is said that the resulting damage in the Bruch's membrane, which were incurred by the irradiation of the 647 nm laser light, is very effective for the incidence of ocular neovascular vessels. Thereby, there were induced the experimental choroidal neovascular vessels (abbreviated as CNV). The induced CNV are the neovascular vessels as branched from the choroidal normal vascular vessels in the ocular fundus. Such CNV have infiltrated in the subretinal space, namely the space between the sensory retina and choroids, to involve the occurrence of exudation, bleeding and retinal detachment. The formation of the neovasculature lesions comprising the CNV was confirmed by a process which comprised intravenously injecting fluorescein or indocyanine green to the so treated monkeys and subsequently carrying out the diagnosis method according to a fluorescence fundus angiography of the ocular fundus. It was thus confirmed that a great number of the neovasculature lesions comprising the experimental CNV could be produced in the subretinal space.

(i) To the monkeys which had the neovasculature lesion comprising the CNV so produced by the modified Ryan's method in the subretinal space of the ocular fundus, was intravenously administered mono-L-aspartyl chlorin e6 tetra-sodium salt (sometimes abbreviated as NPe6 hereinafter) at a dose of 20 mg/kg at a vein in the lower limbs. Then, using a scanning laser ophthalmoscope (abbreviated as SLO; manufactured by Rodenstock, Co., Germany) which emits a beam of argon laser light of a wavelength of 488 nm, a beam of 488 nm argon laser light was continuously irradiated to the ocular fundus for 10 minutes, immediately after the time of the intravenous injection of NPe6. By the excitation of NPe6 under irradiation of the 488 nm laser light beam, the NPe6 having distributed in the fundus tissues and in the vascular walls of the ocular fundus could emit a red fluorescence.

In the course of said irradiation of 488 nm laser light beam for 10 minutes, the images of the red fluorescence as emitted in the ocular fundus were recorded by photography on a video tape by means of a high-sensitivity television fundus camera apparatus. Thereafter, at intervals of 10 minutes, a beam of 488 nm laser light was repeatedly irradiated to the ocular fundus each for about one minute. At each of the irradiations of the 488 nm laser light beam, the images of the red fluorescence emitted from the vascular vessels of the ocular fundus were recorded on the video tape. At the time of 60 minutes after the time of the intravenous injection of NPe6, the irradiation of the 488 nm laser light beam was terminated. The images of the fluorescence emitted from the ocular fundus vascular vessels were then reproduced from the recording video tape for the purpose of observation.

According to these observations, it was revealed that the red fluorescence of the NPe6 having distributed and remaining in the vascular walls of the retinal normal vascular vessels was appreciably observable at its prominent intensity, but the red fluorescence of the NPe6 having distributed and remaining in the vascular walls of the choroidal neovascular vessels (CNV) was observable slightly but detectable at its weak intensity, at the time of 7.5 minutes after the time of the intravenous injection of NPe6.

It was also revealed that, at the time of 20 minutes after the time of the intravenous injection of NPe6, the red fluorescence emitted from the NPe6 present in the retinal normal vascular vessels had decreased to a lower and hardly detectable intensity, but the red fluorescence emitted from the NPe6 present in the choroidal neovascular vessels (CNV) was confirmed to remain at a higher and prominently observable intensity. From these observations, it was revealed that NPe6 had accumulated and remained selectively in the vascular walls of the choroidal neovascular vessels still at said time of 20 minutes after the injection of NPe6. Accordingly, it was found that the NPe6, which was once distributed in the vascular walls of the retinal normal vascular vessels after the intravenous injection of NPe6, could be substantially entirely cleared or eliminated from the vascular walls of the retinal normal vascular vessels already at the time of 20 minutes after the intravenous injection of NPe6, and that the NPe6 as once distributed could be accumulated and remain preferentially in the vascular walls of the choroidal neovascular vessels (CNV), in contrast.

It was further found that, at the time of 60 minutes after the intravenous injection of NPe6, the red fluorescence emitted from the NPe6 present in the retinal normal vascular vessels was never observable with any of the fluorescence images as reproduced from said recording video tape, but the red fluorescence of the Npe6 present in the choroidal neovascular vessels (CNV) could be observed at a high and prominent intensity. Consequently, it has been confirmed that the NPe6 can accumulate and remain at a significant concentration preferentially in the vascular walls of the neovascular vessels (CNV) in the ocular fundus.

At the time of 65 to 70 minutes after the time of the intravenous injection of NPe6, three eyeballs were enucleated from the monkey under test, and each eyeball was cut into 4 pieces. These cut pieces of the eyeballs were frozen in a bath of liquid nitrogen. Cross-section samples each having a thickness of 5 µm were prepared from the ocular fundus tissue region of the frozen pieces of the eyeballs. These cross-section samples were placed under an excitation light of a wavelength of 380 to 420 nm, and the red fluorescence emitted from the NPe6 remaining in said samples was observed under a fluorescence microscope. The red fluorescence was almost not observable in the cross-section samples as prepared from the retinal parenchymal region of the ocular fundus. In the cross-section samples containing the retinal normal vascular vessels, only a very slight degree of the red fluorescence was observed at the retinal normal vascular vessels present therein. In contrast, in the cross-section samples containing the choroidal neovascular vessels (CNV), the red fluorescence emitted from the choroidal neovascular vessels was observed confirmably at a significant intensity.

Accordingly, it has been confirmed that, when NPe6 is intravenously administered to the test monkeys at a dose of 20 mg/kg, the administered NPe6 can accumulate and remain at a significant concentration preferentially in the vascular walls of the choroidal neovascular vessels, but a substantial major part of NPe6 can have been cleared or eliminated completely from the vascular walls of the retinal normal vascular vessels of the ocular fundus already at the time of 60 minutes after the intravenous injectionof NPe6.

(ii) NPe6 was intravenously administered at a dose of 0.5 mg/kg or 1.0 mg/kg in the same way as described in the above (i), to the test monkeys having the neovasculature lesions comprising the CNV as produced by the above described method, within the retina of the ocular fundus.

In the same way as described in the above (i), a beam of a laser light of 488 nm-wavelength was irradiated by SLO at an enhanced fluence to the ocular fundi of the test monkeys continuously for 10 minutes immediately after the time of the intravenous injection of NPe6. At the time of 15 minutes after the time of the intravenous injection of NPe6, the irradiation of the beam of 488 nm-laser light to the ocular fundi was again started and effected for a duration of 10 minutes. During this 10 minutes-irradiation of the 488 nm-laser light to the ocular fundi, the images of the red fluorescence emitted from the ocular fundi were recorded by photography on a video tape by means of a high-sensitivity television fundus camera.

The images as recorded of the red fluorescence were reproduced from the photographs in the recording video tape and then were visually observed. According to these observations, it has been found that the red fluorescence emitted from the NPe6 present in the retinal normal vascular vessels has substantially entirely been eliminated and disappeared, but the red fluorescence emitted from the NPe6 present in the choroidal neovascular vessels can be confirmably observed at a slight but appreciable intensity at the time point of 20 minutes after the time of the intravenous injection of NPe6, in a case when NPe6 was injected at a dose of 0.5 mg/kg. Additionally, it has been found that the red fluorescence emitted from the NPe6 present in the retinal normal vascular vessels has substantially entirely been eliminated, but the red fluorescence emitted from the NPe6 present in the choroidal neovascular vessels can be confirmed at a significant and appreciable intensity at the time point of 30 minutes after the time of the intravenous injection of NPe6, in a case when NPe6 was injected at a dose of 1.0 mg/kg.

TEST EXAMPLE 2

This Example illustrates an embodiment of the method of the first aspect of this invention.

In the experiments of this Test Example 2, there were used 31 neovasculature lesions chosen from among the neovasculature lesions which comprised the experimental choroidal neovascular vessels (CNV) as produced in the ocular fundi of the monkeys of the genus *Macaca* by the modified Ryan's method set out in the Test Example 1 above.

A solution of mono-L-aspartyl chlorin e6 tetra-sodium salt (sometimes abbreviated as NPe6) dissolved in physiological saline at a concentration of 5.0 mg/ml was intravenously administered at a vein in the lower limbs of the test monkeys having the experimental CNV. The dose of the administration of NPe6 was preset at 0.5 mg/kg, 1 mg/kg, 2 mg/kg or 10 mg/kg.

At the time of 10 minutes after the time of the intravenous injection of NPe6, the operation for irradiation and scanning of a beam of the laser light of 488 nm-wavelength was started to be effected towards the ocular retina. During this irradiation of the 488 nm-laser light, the images of the red fluorescences emitted from the retinal normal vascular vessels and from the choroidal neovascular vessels were observed by an apparatus for the fluorescence ocular fundus angiography of the ocular fundus (namely, an infrared light fundus camera).

When NPe6 was intravenously injected at a dose of 0.5 mg/kg, it was observed that the red fluorescence of NPe6 had been substantially entirely eliminated from the retinal normal vascular vessels already at the time point of 20 minutes after the time of the intravenous injection of NPe6, but the red fluorescence of the NPe6 present in the neovasculature lesions comprising CNV was confirmed to continue to emit still at said time point of 20 minutes. At said time of 20 minutes after the time of the injection of NPe6, irradiation of 664 nm-laser light as emitted from a semiconductor-type laser-generator [manufactured by Matsushita Industry System, Co., Ltd., Japan] was started to be effected as a laser-irradiating spot of 1 mm diameter selectively to only one of the said lesions under test. The 664 nm-laser light was irradiated for 300 seconds at a fluence of 204 J/cm$^2$. The details of the experimental conditions for this irradiation of the 664 nm-laser light are shown in Table 1 given hereinafter.

When NPe6 was intravenously injected at a dose of 1 mg/kg, it was observed that the red fluorescence of the administered NPe6 present in the retinal normal vascular vessels had substantially entirely been eliminated but the red fluorescence of the NPe6 present in the neovasculature lesions was confirmed to continue to emit at the time point of 30 minutes after the time of the intravenous injection of NPe6. The observations of the red fluorescence of NPe6 were made by the apparatus for the fluorescence ocular fundus angiography of the ocular fundus. At said time point of 30 minutes after the NPe6 injection, irradiation of the 664 nm-laser light was started to be effected as a laser-irradiating spot of 1 mm diameter selectively to 3 lesions chosen from among the neovasculature lesions under test. The laser light was irradiated for 60 to 300 seconds at different fluences. The details of the experimental conditions for these irradiations of the 664 nm-laser light are shown in Table 1 below.

When NPe6 was intravenously injected at a dose of 2 mg/kg or 10 mg/kg, it was observed that the red fluorescence of the NPe6 present in the retinal normal vascular vessels had substantially entirely been eliminated, but the red fluorescence of the NPe6 present in the neovasculature lesions was confirmed by said fluorescence ocular fundus angiography apparatus to continue to emit still at the time point of 60 minutes after the time of the NPe6 injection. At said time of 60 minutes after the time of the injection of NPe6, irradiation of the 664 nm-laser light was started to be effected to the neovasculature lesions. At the dose of 2 mg/kg of NPe6, two neovasculature lesions were irradiated with the 664 nm-laser light. At the dose of 10 mg/kg of NPe6, four neovasculature lesions were irradiated with the 664 nm-laser light. The 664 nm-laser light was irradiated at different fluences for 60 seconds or for 10 seconds. The details of the experimental conditions for these irradiations of the 664 nm-laser light are shown in Table 1.

In the above experiments, the irradiations of the 664 nm-laser light were designed to be carried out under such experimental conditions that the laser light was irradiated at an irradiance of 0.57 to 0.75 $W/cm^2$, for a duration of 10 to 300 seconds, and at a fluence of 7.5 to 204 $J/cm^2$.

Among the 31 neovasculature lesions comprising CNV as employed in the tests, 13 neovasculature lesions were treated by the administration of NPe6 but without irradiation of the 664 nm-laser light and were referred to as First Control group. While, 8 neovasculature lesions were treated by the irradiation of the 664 nm-laser light but without administration of NPe6 and were referred to as Second Control group.

After the treatment with the irradiation of 664 nm-laser light was terminated, the test monkeys having the neovasculature lesions, either treated or untreated, were fed for 1 week under routine feeding conditions. After the feeding for one week, the effects of the above treatments were judged by a fluorescence fundus angiography with fluorescein and by a fluorescence fundus angiography with indocyanine green (ICG). For the fluorescein fundus angiography, the ocular fundi of the monkeys were observed and diagnosed by means of an ocular fundus camera apparatus made by Nikon Company, Japan, after the intravenous injection of fluorescein. For the fluorescence fundus angiography with ICG, the ocular fundi of the monkeys were observed and diagnosed by means of SLO or by means of an infrared light fundus camera apparatus for the infrared ocular fundus angiography, after the intravenous injection of ICG. Examinations were made of changes which have occurred in the treated neovasculature lesions and also in the retinal parenchymal tissue and in the retinal normal vascular vessels around the neovasculature lesions in the ocular fundus. In account of the so examined changes occurred in the fundus, the therapeutic effects of the treatments as conducted were judged. In the above experiments, it was confirmed that, in the totally 10 neovasculature lesions which were treated by both of the administration of NPe6 and the irradiation of 664 nm-laser light, the vascular lumens of the CNV present in said 10 neovasculature lesions could be occluded without involving any substantial injury in the tissues present in the surrounding regions positioned outside said 10 neovasculature lesions, and without involving any substantial injury in the retinal normal vascular vessels. It is thus confirmed that the method of the first aspect of this invention is able to selectively occlude with success all the CNV present in the above-mentioned 10 neovasculature lesions which have been treated with a combination of the administration of NPe6 and the irradiation of 664 nm-laser light.

On the other hand, in the totally 21 neovasculature lesions of the First Control group and of the Second Control group, it was observed that any of the CNV as treated could not be occluded.

Then, several speciemen fragments were excised out of the ocular fundus tissues containing the regions of the neovasculature lesions comprising the CNV which had been selectively occluded by the method of this invention in the above experiments. These speciemen fragments of the ocular fundus tissues were then pathologically examined under an optical microscope. From the microscopic examination, it was shown that the vascular lumens of the choroidal neovascular vessels (CNV), which were selectively occluded by the method of this invention, were filled and occluded with cellular debris, and that the retinal normal vascular vessels and the choroidal normal vascular vessels which are positioned adjacently to the choroidal neovascular vessels (CNV) as selectively occluded by the method of this invention, were remaining intact or nearly intact. Additionally, it was shown that the biological structure of the retinal inner layer, which is adjacent to the so treated choroidal neovascular vessels (CNV), remained unchanged.

An electron microscopic examination of the CNV which were selectively occluded by the method of this invention in the above experiments, has revealed that the endothelial cells present in the vascular walls of the selectively occluded CNV had been severely damaged, resulting in deterioration of the normal structure of the endothelial cells. It was also revealed that the vascular lumens of the so selectively occluded CNV were embedded with the cytoplasmic debris and/or with blood cell-deteriorated components. While, it was seen that the retinal normal vascular vessels and the choroidal normal vascular vessels which are adjacent to the selectively occluded CNV were not injured. Accordingly, it is assumed that the selective occlusion of CNV which is attainable in accordance the method of this invention can be resulted due to the injury as incurred in the endothelial cells of the vascular walls of the neovascular vessels of CNV.

The experimental conditions for the irradiation of the 664 nm-laser light as effected in this Test Example 2, as well as the results of the PDT treatments for the selective occlusion of CNV are summarized in Table 1 below. In Table 1, NPe6 is the abbreviation of mono-L-aspartyl chlorin e6 tetra-sodium salt.

to the manners or patterns in which the changes in the concentrations of mono-L-aspartyl chlorin e6 tetra-sodium salt (NPe6) (as given at a dose of 0.5 to 10 mg/kg) having

TABLE 1

| Test Run No. | NPe6 dose (mg/kg) | Time point for starting irradiation of 664 nm-laser light, namely lapse time (in minutes) after administration of NPe6 | Irradiance of 664 nm-laser light (W/cm$^2$) | Duration of irradiation of 664 nm-laser light (seconds) | Fluence of 664 nm-laser light (J/cm$^2$) | Number of CNV lesions tested | Number of CNV lesions containing the selectively occluded CNV after irradiation of 664 nm-laser light |
|---|---|---|---|---|---|---|---|
| 1 | 10 | 60 | 0.75 | 10 | 7.5 | 4 | 4 |
| 2 | 2 | 60 | 0.75 | 60 | 45 | 2 | 2 |
| 3 | 1 | 30 | 0.57 | 60 | 34.2 | 1 | 1 |
|   | 1 | 30 | 0.57 | 180 | 102.6 | 1 | 1 |
|   | 1 | 30 | 0.57 | 300 | 171 | 1 | 1 |
| 4 | 0.5 | 20 | 0.68 | 300 | 204 | 1 | 1 |
| First control group | 10 | — | — | — | — | 4 | 0 |
|   | 2 | — | — | — | — | 2 | 0 |
|   | 1 | — | — | — | — | 3 | 0 |
|   | 0.5 | — | — | — | — | 4 | 0 |
| Second control group | 0 | 60 | 0.75 | 10 | 7.5 | 4 | 0 |
|   | 0 | 60 | 0.75 | 60 | 45 | 2 | 0 |
|   | 0 | 60 | 0.75 | 300 | 225 | 2 | 0 |

TEST EXAMPLE 3

Referential Example 2

In this Example, experiments were carried out to examine and detect that, when indocyanine green (ICG) [which is commonly used as an infrared fluorescence agent in the infrared fluorescence fundus angiography for diagnosing the ocular fundus of patients with age-related macular degeneration] had been intravenously injected at a dose of 0.5 to 1 mg/kg into the monkeys having the experimental choroidal neovascular vessels (CNV) in the ocular fundus of eye, the concentration of ICG having uptaken, distributed and remaining in the vascular walls of the retinal normal vascular vessels, as well as the concentration of ICG having uptaken, distributed and remaining in the vascular walls of the choroidal neovascular vessels (CNV) in the ocular fundus of the monkeys were time-dependently changing in different manners or patterns from each other.

In these experiments, the time-dependent changes in the concentrations of ICG having distributed and remaining in the vascular walls of the retinal normal vascular vessels and in the vascular walls of the choroidal neovascular vessels (CNV) in the ocular fundus of the monkeys were examined by a process wherein a beam of laser light containing a light of 790 nm-wavelength (as emitted from a semiconductor type laser generator) was used as an excitation light, and wherein the changes in the intensity of the infrared fluorescence emitted from the ICG as excited within said vascular walls were continuously recorded by photographs by means of an infrared light fundus camera apparatus (of modified TCR 50-IA type, manufactured by Topcon Co., Japan) for the infrared fluorescence fundus angiography for diagnosing the ocular fundus, and wherein the photographed images of the fundus were observed visually.

From these experiments, it has now been found that the manners or patterns of the time-dependent changes in the concentrations of ICG having distributed and remaining in the vascular walls of the retinal normal vascular vessels and in the vascular walls of the choroidal neovascular vessels (CNV) in the ocular fundus of the monkeys having received the administration of ICG are always very much analogous to distributed and remaining in the vascular walls of the retinal normal vascular vessels and in the vascular walls of the choroidal neovascular vessels (CNV) of the monkeys took place time-dependently, as shown by the test results obtained in the above Test Example 1.

Details of the experimental procedures in this Test Example 3 are as follows.

In the same manner as in the above Test Example 1, the neovasculature lesions comprising the experimental choroidal neovascular vessels (CNV) were produced in the ocular fundi of monkeys of the genus *Macaca*, according to the modified Ryan's method.

An aqueous solution of ICG dissolved in distilled water for the injections at a concentration of 5.0 mg/ml of ICG was intravenously injected at a dose of ICG of 0.5 mg/kg at a vein in the lower limbs of the monkeys having the neovasculature lesions in the retina of the eye.

Immediately after the time of the intravenous injection of ICG, the ocular fundi of the monkeys were continuously observed under irradiation of the beam of laser light containing a light of 790 nm-wavelength by means of an infrared light camera apparatus (of a modified TCR 50-IA type, manufactured by Topcon Co.) for infrared fluorescence fundus the angiography for diagnosing the ocular fundus.

At a time point of about 7 to 8 minutes after the time of the intravenous injection of ICG, the infrared fluorescence of ICG was observed at a prominent and appreciable intensity in the retinal normal vascular vessels, and at said time point, the ophthalmologist can commence to observe that the infrared fluorescence of ICG was emitted also in the choroidal neovascular vessels (CNV) at a slight but appreciable intensity. Subsequently, the intensity of the infrared fluorescence of ICG emitted in the CNV was increasing with the time lapse.

At the time point of 20 minutes after the time of the administration of ICG, the intensity of the infrared fluorescence of ICG in the retinal normal vascular vessels had decreased, while the intensity of the infrared fluorescence of ICG emitted in the CNV had increased to a prominent and appreciable intensity which was confirmable by the observer.

TEST EXAMPLE 4

This Example illustrates an embodiment of the method of the second aspect of this invention.

(a) The test monkeys having the experimental CNV in the subretinal space of the ocular fundus, which were employed in the above Test Example 3, were again used in this Test Example 4 as test animals. To these test monkeys was intravenously injected ICG at a dose of 1 mg/kg in the same way as in Test Example 3. Immediately after the time of the intravenous injection of ICG, the ocular fundi of the monkeys were continuously observed by means of an infrared light fundus camera apparatus (of modified TCR 50 type, manufactured by Topcon Co., Ltd.) for the infrared fluorescence fundus angiography for diagnosing the ocular fundus. The observation with the fundus camera was made under irradiation of the ocular fundi with the laser light containing a light of 790 nm-wavelength. There was recorded the time point at which the infrared fluorescence of ICG was eliminated entirely from the retinal normal vascular vessels. The time-gap which was extended between the aforesaid time point as recorded for the entire elimination of the infrared fluorescence of IGC and the time of the intravenous injection of ICG was calculated in a unit of "minutes" or "second", whereby it was estimated that said time-gap was 30 minutes.

(b) Time was allowed to pass until the infrared fluorescence of ICG was eliminated entirely from the neovasculature lesions in the ocular fundi of the test monkeys. Thereafter, a volume of an aqueous solution of mono-L-aspartyl chlorin e6 tetra-sodium salt (NPe6) dissolved in physiological saline at a concentration of 5 mg/ml of NPe6 was intravenously injected at a vein in the lower limbs of the monkeys so that NPe6 was given at a dose of 1 mg/kg.

(c) At a time point of 30 minutes after the time of the intravenous injection of NPe6, it was started to irradiate a beam of laser light of 664 nm-wavelength (as emitted from a semiconductor-type laser generator, manufactured by Matsushita Industry System, Co. Ltd., Japan) in the form of a laser-irradiating spot of 1 mm diameter to 3 lesions of the neovasculature lesions under test. The 664 nm-laser light as irradiated was irradiated at an irradiance of 0.57 $W/cm_2$ for 180 seconds so that the fluence was of 102.6 $J/cm^2$.

After the terminated irradiation of the 664 nm-laser light, the test monkeys were fed under routine feeding conditions for one week. Thereafter, the effects of the PDT treatments were judged in the same way as in the above Test Example 2, by the fluorescence fundus angiography with fluorescein and by the fluorescence fundus angiography with ICG. It was found that the CNV present in the 3 neovasculature lesions as treated with the laser irradiation were successfully occluded, while the retinal normal vascular vessels which were adjacent to the so treated neovasculature lesions, as well as the retinal parenchymal tissue and the choroidal normal vascular vessels present in the surrounding regions in the retina could remain intact. Accordingly, it was found in this Example that the CNV present in the neovasculature lesions could selectively be occluded, with success.

TEST EXAMPLE 5

This Example illustrates an embodiment of the method of the third aspect of this invention.

(a) Indocyanine green (ICG) was dissolved at a concentration of 10 mg/ml in a volume of physiological saline, and mono-L-aspartyl chlorin e6 tetra-sodium salt (NPe6) was dissolved at a concentration of 10 mg/ml in a further volume of physiological saline. The resulting two solutions were mixed together in the equal proportions, to prepare an aqueous solution usable for the intravenous injection of ICG and NP6. Monkeys, which had the experimental CNV in the subretinal space of the ocular fundus as produced by the modified Ryan's method described in the above Test Example 1, were used in this Test Example 5 as test animals.

The above-mentioned aqueous solution of ICG and NPe6 usable for the intravenous injection as prepared in the above was intravenously injected to the test monkeys in the same way as in the above Test Example 3. It was prescribed that the dose of ICG was 0.5 mg/kg and the dose of NPe6 was 0.5 mg/kg upon the injection of them.

Immediately after the time of the intravenous injection of ICG and NPe6, the ocular fundi of the test monkeys were continuously photographed and observed under irradiation of the laser light containing a light of 790 nm-wavelength, by means of the infrared light fundus camera apparatus (of a modified TCR50-IA-type, manufactured by Topcon Co., Ltd.) for the fluorescence fundus angiography of diagnosing the ocular fundus, in the same way as in Test Example 3.

At a time point of about 7 to 8 minutes after the time of the intravenous injection of ICG and NPe6, the infrared fluorescence of ICG was observed at a prominent and appreciable intensity in the retinal normal vascular vessels. At a time point of 20 minutes after the time of the intravenous injection of ICG and NPe6, it was observed that the infrared fluorescence of ICG in the retinal normal vascular vessels had decreased to a poor intensity, while the infrared fluorescence was retained at a prominent and apreciable intensity in the vascular walls of CNV present in the neovasculature lesions under observation.

(b) At said time point of 20 minutes after the time of the intravenous injection of ICG and NPe6, the irradiation of the laser light of 664 nm-wavelength was started in the form of laser-irradiating spot of 1 mm diameter to 3 lesions of the neovasculature lesions in the monkeys under test, in the same way as in the above Test Example 4, (c). The 664 nm-laser light as irradiated was irradiated at an irradiance of 0.68 $W/cm^2$ for 300 second so that the fluence was of 204 $J/cm^2$.

After the terminated irradiation of the 664-nm laser light, the test monkeys were fed under routine feeding conditions for one week. Thereafter, the effects of the above PDT treatments were judged in the same way as in the above Test Example 2, by the fluorescence fundus angiography with fluorescein and by the fluorescence fundus angiography with indocyanine green (ICG). It was found that the CNV present in the 3 neovasculature lesions comprising CNV as treated with the laser irradiation had been occluded successfully, while the retinal normal vascular vessels which were adjacent to the so treated neovasculature lesions, as well as the retinal parenchymal tissue and the choroidal normal vascular vessels present in the surrounding region in the retina could remain intact. Accordingly, it was revealed also in this Example that the CNV present in the neovasculature lesions could selectively be occluded with success.

Example 1 for Formulation 100 mg of mono-L-aspartyl chlorin e6 tetra-sodium salt was dissolved in 4 ml of distilled water ready for injections. The resulting aqueous solution was then adjusted to pH 7.4. After the aseptic filtration thereof, the resulting sterilized solution was lyophilized in vials. The resulting lyophilized preparation may be dissolved in an appropriate volume of physiological saline, before its use.

Example 2 of Formulation 10 mg/ml of ICG was dissolved in a volume of sterile physiological saline at a concentration of 10 mg/ml. Further, mono-L-aspartyl chlorin e6 tetra-sodium salt was dissolved in a further volume of physiological saline at a concentration of 10 mg/ml. The resultant two aqueous solutions were mixed together in the equal proportions. The resulting solution of ICG and NPe6 is suitable for the intravenous injection of ICG and NPe6 in order to carry out the method of the third aspect of this invention.

INDUSTRIAL APPLICABILITY

As described hereinbefore, in short, this invention provides a method for selectively occluding the neovascular vessels in the ocular fundus, which comprises intravenously administering mono-L-aspartyl chlorin e6 or a salt thereof, particularly the tetra-sodium salt thereof at a dose of 0.5 to 10 mg/kg to a patient; subsequently estimating an appropriate timing, that is, the time point when mono-L-aspartyl chlorin e6 substance as administered has decreased in or has been eliminated from the retinal normal vascular vessels of the ocular fundus of the patient but still has accumulated and is remaining at a significant and appreciable concentration in the vascular walls of the neovascular vessels in the ocular fundus; starting at an appropriate time point so estimated to irradiate a laser light of 664 nm-wavelength; and irradiating the 664 nm-laser light to the neovasculature lesions comprising the neovascular vessels, at a certain controlled fluence.

By this invention, it is made feasible to occlude selectively such neovascular vessels in the ocular fundus which can be formed in diseases having the incidence of choroidal neovascular vessels, for example, age-related macular degeneration, and which can be formed in diseases having the incidence of retinal neovascular vessels, for example, proliferative diabetic retinitis. Thus, this invention is useful for therapeutic treatment of said ophthalmological diseases.

What is claimed is:

1. A photodynamic therapy method for selectively occluding vessels comprising choroidal neovascular vessels and retinal neovascular vessels formed in a mammal having an ocular fundus tissue comprising retinal normal parenchymal tissue, retinal normal vascular vessels, choroidal normal vascular vessels lying under the retina, choroidal neovascular vessels and retinal neovascular vessels, said method comprising:

(a) administering intravenously a photosensitizer comprising a chlorin e6 compound selected from the group consisting of a mono-L-aspartyl chlorin e6 and a pharmaceutically acceptable salt thereof, to the mammal at a dose of 0.5 mg/kg to 10 mg/kg calculated on the weight basis of the photosensitizer;

(b) allowing the photosensitizer to be carried along by the blood stream circulating in the ocular retinal central artery and ciliary artery, to be taken up by the endothelial cell layers of the retinal normal vascular vessels, the endothelial cell layers of the choroidal normal vascular vessels, and the endothelial cell layers of the retinal neovascular vessels and/or the endothelial cell layers of the choroidal neovascular vessels, and allowing the photosensitizer to be distributed and accumulated in and being eliminated or cleared from the vascular walls of the normal vascular vessels and the neovascular vessels;

(c) subsequently irradiating and scanning, using a laser light at a 488 nm wavelength at a sufficient power, intermittently or continuously, through the surface of ocular cornea, pupil, lens and vitreous fluid of the eye of the mammal, to and on the ocular fundus tissue of the mammal, so as to photo-excite the photosensitizer, thereby inducing emission of a red fluorescence from the now photo-excited photosensitizer having been distributed in the vascular walls of the normal vascular vessels and in the vascular walls of the neovascular vessels in the ocular fundus tissue; and further observing intermittently or continuously the intensity of the red fluorescence which is emitted from the photo-excited photosensitizer by using a fluorescence ocular fundus angiography apparatus or a fluorescence microscope for funduscopy;

(d) using the fluorescence ocular fundus angiography apparatus or fluorescence microscope for funduscopy during the irradiation of the 488 nm-wavelength laser light, to estimate a time point at which, in the course of the elimination or clearance of the photosensitizer out of the vascular walls of the retinal normal vascular vessels and the choroidal normal vascular vessels, the intensity of the red fluorescence emitted from the photosensitizer present in the vascular walls of the retinal normal vascular vessels under observation can be observed to have decreased to a lowered value of about one-half-fold or less of the intensity of the red fluorescence emitted from the photosensitizer remaining in the vascular walls of the neovascular vessels under observation; and thus establishing an estimated time point when the concentration of the photosensitizer present in the vascular walls of the retinal normal vascular vessels under observation has decreased to a lowered value of about one-half-fold or less;

(e) at the estimated time point provided in said step (d) or within 1 to 10 minutes from the estimated time point; starting to irradiate a laser light of 664 nm-wavelength in the form of a thin laser beam, via the cornea, pupil and vitreous fluid of the eye, exclusively to targeted lesions comprising the neovasculature formed of the neovascular vessels in the ocular fundus, in such a way that the laser light of 664 nm-wavelength is irradiated at a power necessary to excite the photosensitizer remaining in the vascular walls of the neovascular vessels; and (f) subsequently permitting the lumens of the neovascular vessels contained in the lesions as irradiated with the laser light of 664 nm-wavelength to be occluded by the developed actions of the photochemical reaction of the laser-excited photosensitizer remaining in the vascular walls of the neovascular vessels, whereby a selective occlusion of the choroidal neovascular vessels and/or the retinal neovascular vessels is achieved.

2. The method according to claim 1, wherein, in said step (e) of the method, the irradiation using the laser light of 664 nm-wavelength is started at a time point when a time period of 10 to 70 minutes has lapsed after the time of the intravenous injection of the photosensitizer; and said time point is also at least the estimated time point determined in step (d).

3. The method according to claim 1, wherein, the estimated time point determined in said step (d) is 20 to 70 minutes from the time of the intravenous injection of the photosensitizer; and that said estimated time point is also such time point when it can be determined from the observation with the fluorescence ocular fundus angiography apparatus or fluorescence microscope for funduscopy during the irradiation of the 488 nm-wavelength laser light, that the intensity of the red fluorescence emitted from the photosensitizer remaining in the vascular walls of the choroidal neovascular vessels and/or the retinal neovascular vessels has reached its peak value under the irradiation of the laser light of 488 nm-wavelength; and that said estimated time point is further such time point when it is additionally observed by said fluorescence ocular fundus angiography apparatus or fluorescence microscope, that the red fluorescence as emitted from the photosensitizer still remaining in the vascular walls of the retinal normal vascular vessels has disappeared completely during the irradiation of the laser light of 488 nm-wavelength, and wherein, at the estimated time point, the laser light of 664 nm-wavelength is then started in said step (e) exclusively targeting lesions comprising the neovasculature formed of the neovascular vessels in the ocular fundus.

4. A method according to claim 1, wherein the laser light of 664 nm-wavelength, which is irradiated to the targeted lesions comprising the neovascular vessels in the ocular fundus, has an irradiance of 10 to 1500 mW/cm$^2$, on the top retina face, as measured at the corneal surface by means of an optical power meter, and said laser light of 664 nm-wavelength is irradiated for a duration of 10 to 300 seconds and at a fluence of the laser light in a range of 7.0 J/cm$^2$ to 250 J/cm$^2$, provided that said fluence of the laser light is evaluated by multiplying the laser irradiance (in W/cm$^2$) by the duration of the laser irradiation (in seconds), and wherein the lower is the dose of mono-L-aspartyl chlorin e6, the fluence of the laser light to be irradiated is controlled to be the higher, so as to achieve the selective occlusion of the neovascular vessels present in the targeted lesions.

5. A method according to claim 1, wherein the laser light of 664 nm-wavelength is started in the step (e) of the method to be irradiated at such a time point when a time period of 20 to 70 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 0.5 mg/kg to 10.0 mg/kg (as calculated on the weight basis of mono-L-aspartyl chlorin e6 tetra-sodium salt, namely NPe6; and the same way of this calculation is applied hereinafter), and wherein the fluence of the laser light of 664 nm-wavelength to be irradiated is controlled within a range of 7 J/cm$^2$ to 205 J/cm$^2$.

6. A method according to claim 1, wherein the laser light of 664 nm-wavelength is started in the step (e) of the method to be irradiated at such a time point when a time period of 20 to 30 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 0.5 mg/kg to 0.9 mg/kg (as calculated on the weight basis of NPe6), and wherein the fluence of the laser light of 664 nm-wavelength to be irradiated is controlled within a range of 175 J/cm$^2$ to 205 J/cm$^2$.

7. A method according to claim 1, wherein the laser light of 664 nm-wavelength is started in the step (e) of the method to be irradiated at such a time point when a time period of 30 to 60 minutes has lapsed after the time of the intravenous administration of mono-L-aspartyl chlorin e6 or a salt thereof, as long as the chlorin e6 compound is given at a dose of 1 mg/kg to 1.9 mg/kg (as calculated on the weight basis of NPe6), and wherein the fluence of the laser light of 664 nm-wavelength to be irradiated is controlled within a range of 30 J/cm$^2$ to 175 J/cm$^2$.

8. A method according to claim 1, wherein the laser light of 664 nm-wavelength is started in the step (e) of the method to be irradiated at such a time point when a time period of 60 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 2 mg/kg to 9.5 mg/kg (as calculated on the weight basis of NPe6), and wherein the fluence of the laser light of 664 nm-wavelength to be irradiated is controlled within a range of 30 J/cm$^2$ to 45 J/cm$^2$.

9. A method according to claim 1, wherein the laser light of 664 nm-wavelength is started in the step (e) of the method to be irradiated at such a time point when a time period of 60 to 70 minutes has lapsed after the time of the intravenous administration of mono-L-aspartyl chlorin e6 or a salt thereof, as long as the chlorin e6 compound is given at a dose of 9.5 mg/kg to 10 mg/kg (as calculated on the weight basis of NPe6), and wherein the fluence of the laser light of 664 nm-wavelength to be irradiated is controlled within a range of 7 J/cm$^2$ to 9 J/cm$^2$.

10. A method according to claim 1, wherein the mammalian animal to be treated is a human having suffered from age-related macular degeneration with the choroidal neovascular vessels.

11. A method according to claim 1, wherein the mammalian animal to be treated is a human having suffered from proliferative diabetic retinitis with proliferative neovascular vessels in the retina.

12. A photodynamic therapy method for selectively occluding various ocular vessels comprising choroidal neovascular vessels, and/or retinal neovascular vessels formed in a mammal having an ocular fundus tissue comprising retinal normal parenchymal tissue, retinal normal vascular vessels, choroidal normal vascular vessels lying under the retina, and choroidal neovascular vessels and retinal neovascular vessels, said method comprising:

(a) administering initially indocyanine green intravenously to the mammal at a dose of 0.5 mg/kg to 1 mg/kg;

(b) allowing the indocyanine green to be carried along by the blood stream circulating in the ocular retinal central artery and ciliary artery, to be uptaken in the endothelial cell layers of the retinal normal vascular vessels, in the endothelial cell layers of the choroidal normal vascular vessels, in the endothelial cell layers of the choroidal neovascular vessels and/or the endothelial cell layers of the retinal neovascular vessels, and allowing the indocyanine green to be distributed and accumulated in and being eliminated or cleared from the vascular walls of the normal vascular vessels and the neovascular vessels;

(c) subsequently irradiating and scanning using a laser light having a 790 nm-wavelength at a sufficient power, intermittently or continuously, through the surface of ocular cornea, pupil, lens and vitreous fluid of the eye, to and on the ocular fundus tissue of the mammal, so as to photo-excite the indocyanine green inducing emission of an infrared fluorescence from the now photo-excited indocyanine green having been distributed in the vascular walls of the normal vascular vessels and in the vascular walls of the neovascular vessels in the ocular fundus tissue; and further observing intermittently or continuously the intensity of the infrared fluorescence emitted from the now photo-excited indocyanine green using a fluorescence ocular fundus angiography apparatus or a fluorescence microscope for funduscopy;

(d) using the fluorescence ocular fundus angiography apparatus or fluorescence microscope during the irradiation of the 790 nm-laser light of said step (d), to estimate a time point at which, in the course of the elimination or clearance of indocyanine green out of the vascular walls of the retinal normal vascular vessels and the choroidal normal vascular vessels, the intensity of the infrared fluorescence emitted from the indocyanine green present in the vascular walls of the retinal normal vascular vessels under observation can be observed to have decreased to a lowered value of about one-half-fold or less of the intensity of the infrared fluorescence emitted from the indocyanine green remaining in the vascular walls of the neovascular vessels under observation; and thus establishing an estimated time point at which the concentration of the indocyanine green present in the vascular walls of the retinal normal vascular vessels under observation has decreased to a lowered value of about one-half-fold or less;

(e) calculating a time-gap extending between the time of the first intravenous injection of indocyanine green and the estimated time point determined in said step (d);

(f) allowing time to pass until it can be observed that the infrared fluorescence of the indocyanine green remaining in the vascular walls of the choroidal neovascular vessels and/or retinal neovascular vessels has disappeared completely;

(g) administering a photosensitizer comprising a chlorin e6 compound selected from the group consisting of mono-L-aspartyl chlorin e6 and a pharmaceutically acceptable salt thereof to the mammal intravenously at a dose in a range of 0.5 mg/kg to 10 mg/kg as calculated on the weight basis of NPe6, after said step (f);

(h) allowing the chlorin e6 compound to be carried along by the blood stream circulating in the ocular retinal central artery and ciliary artery, to be uptaken in the endothelial cell layers of the retinal normal vascular vessels, the endothelial cell layers of the choroidal normal vascular vessels, the endothelial cell layers of the choroidal neovascular vessels and/or the endothelial cell layers of the retinal neovascular vessels, and allowing the administered chlorin e6 compound to be distributed and accumulated in and being eliminated or cleared from the vascular walls of the normal vascular vessels and of the neovascular vessels;

(i) permitting the administered chlorin e6 compound to be accumulated and remain in the vascular walls of the choroidal neovascular vessels and/or the retinal neovascular vessels, while the chlorin e6 photosensitizer compound is concurrently eliminated or cleared out of the vascular walls of the normal vascular vessels of the retina and choroid;

(j) at a time point when a time duration, which has a time length equal to that of the time-gap calculated in said step (e), has just passed after the time of the intravenous injection of the chlorin e6 compound; starting to irradiate using a laser light of 664 nm-wavelength in the form of a thin laser beam, via the surface of cornea, pupil and vitreous fluid of the eye, exclusively to targeted lesions comprising the neovasculature formed of the neovascular vessels in the ocular fundus, in such a way that the laser light of 664 nm-wavelength is irradiated at a power necessary to excite the photosensitizer remaining in the vascular walls of the neovascular vessels; and (k) subsequently permitting the lumens of the neovascular vessels contained in the lesions irradiated with the laser light of 664 nm-wavelength to be occluded by the developed actions of the photochemical reaction of the laser-excited photosensitizer remaining in the vascular walls of the neovascular vessels, whereby a selective occlusion of the choroidal neovascular vessels and/or the retinal neovascular vessels is achieved.

13. A method according to claim 12, wherein, in the step (j) of the method, the irradiation of the laser light of 664 nm-wavelength via the surface of cornea, pupil and vitreous fluid of the eye exclusively to the targeted lesions comprising the neovasculatures formed of the neovascular vessels in the ocular fundus is started at such a time point when a time period of 10 to 70 minutes, has lapsed after the time of the intravenous administration of mono-L-aspartyl chlorin e6 or a salt thereof, provided that said time point is the such time point when there has just passed a time duration which has a time length equal to that of the said time-gap as calculated in the step (e) of the method according to claim 12.

14. A method according to claim 12, wherein the laser light of 664 nm-wavelength, which is irradiated to the targeted lesions comprising the neovascular vessels in the ocular fundus, has an irradiance of 10 to 1500 mW/cm$^2$, on the top retina face, as measured at the corneal surface by means of an optical power meter, and the laser light of 664 nm-wavelength is irradiated for a duration of 10 to 300 second, and at a fluence of the laser light in a range of 7.0 J/cm$^2$ to 250 J/cm$^2$, provided that said fluence of the laser light is evaluated by multiplying the laser irradiance (in W/cm$^2$) by the duration of the laser irradiation (in seconds), and wherein the lower is the dose of mono-L-aspartyl chlorin e6, the fluence of the laser light of 664 nm-wavelength to be irradiated is controlled to be the higher, so as to achieve the selective occlusion of the neovascular vessels present in the target lesions.

15. A method according to claim 12, wherein the irradiation of the laser light of 664 nm-wavelength is started in the step (j) of the method at such a time point when a time period of 20 to 70 minutes has lapsed after the time of the intravenous administration of mono-L-aspartyl chlorin e6 or a salt thereof, particularly mono-L-aspartyl chlorin e6 tetrasodium salt, as long as the chlorin e6 compound is given at a dose of 0.5 mg/kg to 10.0 mg/kg (as calculated on the weight basis of NPe6), and wherein the fluence of the laser light of 664 nm-wavelength to be irradiated is controlled within a range of 7 J/cm$^2$ to 205 J/cm$^2$.

16. A method according to claim 12, wherein the irradiation of the laser light of 664 nm-wavelength is started in the step (j) of the method at such a time point when a time period of 20 to 30 minutes has lapsed after the time of the intravenous administration of mono-L-aspartyl chlorin e6 or a salt thereof, particularly mono-L-aspartyl chlorin e6 tetrasodium salt, as long as the chlorin e6 compound is given at a dose of 0.5 mg/kg to 0.9 mg/kg (as calculated on the weight basis of NPe6), and wherein the fluence of the laser light of 664 nm-wavelength to be irradiated is controlled within a range of 175 J/cm$^2$ to 205 J/cm$^2$.

17. A method according to claim 12, wherein the irradiation of the laser light of 664 nm-wavelength is started in the step (j) of the method at such a time point when a time period of 30 to 60 minutes has lapsed after the intravenous administration of mono-L-aspartyl chlorin e6 or a salt thereof, as long as the chlorin e6 compound is given at a dose of 1 mg/kg to 1.9 mg/kg (as calculated on the weight basis of NPe6), and wherein the fluence of the laser light of 664 nm-wavelength to be irradiated is controlled within a range of 30 J/cm$^2$ to 175 J/cm$^2$.

18. A method according to claim 12, wherein the irradiation of the laser light of 664 nm-wavelength is started in the step (j) of the method at such a time point when a time period of 60 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 2 mg/kg to 9.5 mg/kg (as calculated on the weight basis of NPe6), and wherein the fluence of the laser light of 664 nm-wavelength to be irradiated is controlled within a range of 30 J/cm$^2$ to 45 J/cm$^2$.

19. A method according to claim 12, wherein the irradiation of the laser light of 664 nm-wavelength is started in the step (j) of the method at such a time point when a time period of 60 to 70 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 9.5 mg/kg to 10 mg/kg (as calculated on the weight basis of NPe6), and wherein the fluence of the laser light of 664 nm-wavelength to be irradiated is controlled within a range of 7 J/cm$^2$ to 9 J/cm$^2$.

20. A method according to claim 12, wherein the mammalian animal to be treated is a human having suffered from age-related macular degeneration with the choroidal neovascular vessels.

21. A method according to claim 12, wherein the mammalian animal to be treated is a human having suffered from proliferative diabetic retinitis with proliferative neovascular vessels.

22. A photodynamic therapy method for selectively occluding ocular vessels formed in a mammal having ocular fundus tissue and comprising retinal normal parenchymal tissue, retinal normal vascular vessels and choroidal normal vascular vessels lying under the retina, choroidal neovascular vessels and retinal neovascular vessels, said method comprising:

(a) administering intravenously a photosensitizer comprising a chlorin e6 compound selected from the group consisting of mono-L-aspartyl chlorin e6 and a pharmaceutically acceptable salt thereof, to the mammal at a dose of 0.5 mg/kg to 10 mg/kg calculated on the weight basis of the chlorin e6 compound; and injecting intravenously indocyanine green to the mammal at a dose in a range of 0.5 mg/kg to 1 mg/kg, at the same time as or immediately before or after said intravenous administration of the chlorin e6 compound;

(b) allowing the chlorin e6 compound and the indocyanine green to be carried along by the blood stream circulating in the ocular retinal central artery and ciliary artery of the mammal, to be uptaken in the endothelial cell layers of the retinal normal vascular vessels, the endothelial cell layers of the choroidal normal vascular vessels, in the endothelial cell layers of the retinal neovascular vessels, and/or the endothelial cell layers of the choroidal neovascular vessels, and allowing the chlorin e6 compound and indocyanine green to be distributed and accumulated in and being eliminated or cleared from the vascular walls of the normal vascular vessels and of the said neovascular vessels;

(c) subsequently irradiating and scanning using a laser light at a 790 nm wavelength, intermittently or continuously, through the surface of ocular cornea, pupil, lens and vitreous fluid of the eye, to and on the ocular fundus tissue of the animal, so as to induce emission of an infrared fluorescence from the indocyanine green selectively, in the co-presence of the chlorin e6 compound and indocyanine green having been distributed in the vascular walls of the vascular vessels of the ocular fundus tissue; and observing intermittently or continuously, the intensity of infrared fluorescence emitted from the indocyanine green distributed in the vascular walls of the retinal normal vascular vessels, the vascular walls of the choroidal neovascular vessels and/or the vascular walls of the retinal neovascular vessels, using a fluorescence ocular fundus angiography apparatus or a fluorescence microscope for funduscopy;

(d) using the fluorescence ocular fundus angiography apparatus or fluorescence microscope during the irradiation at 790 nm-wavelength, to estimate a time point at which, in the course of the eliminations or clearances of the chlorin e6 compound and indocyanine green from the vascular walls of the retinal normal vascular vessels and the choroidal normal vascular vessels, the intensity of the infrared fluorescence as emitted from the indocyanine green present in the vascular walls of the retinal normal vascular vessels under observation can be observed to have decreased to a lowered value of about one-half-fold or less of the intensity of the infrared fluorescence as emitted from the indocyanine green remaining in the vascular walls of the neovascular vessels under observation; and thus establishing an estimated time point at which the concentration of the chlorin e6 compound present in the vascular walls of the retinal normal vascular vessels under observation has decreased to a lowered value of about one-half-fold or less;

(e) at the estimated time point determined in said step (d) or within 1–10 minutes from the estimated time point; starting to irradiate using a laser light at a 664 nm wavelength in the form of a thin laser beam, via the surface of cornea, pupil and vitreous fluid of the eye, exclusively to targeted lesions comprising neovasculature formed of the neovascular vessels in the ocular fundus, in such a way that the laser light at 664 nm wavelength is irradiated at a power necessary to excite the chlorin e6 compound remaining in the vascular walls of the neovascular vessels; and (f) subsequently permitting that the lumens of the neovascular vessels contained in the lesions irradiated with the laser light at 664 nm wavelength to be occluded by developed actions of a photochemical reaction of the laser-excited chlorin e6 compound remaining in the vascular walls of the neovascular vessels, whereby a selective occlusion of the choroidal neovascular vessels and/or the retinal neovascular vessels is achieved.

23. The method according to claim 22, wherein, said step (e) is started at a time point when a time period of 10 to 70 minutes has lapsed after the time of the intravenous administration of the chlorin e6 compound where said time point is also the estimated time point determined in said step (d).

24. The method according to claim 22, wherein, in said step (d), the estimated time point is 20 to 70 minutes from the time of the intravenous injection of the chlorin e6 compound and the estimated time point is a time point when it can be revealed from the observation with the fluorescence ocular fundus angiography apparatus or fluorescence microscope for funduscopy that the intensity of the infrared fluorescence emitted from the indocyanine green remaining in the vascular walls of the choroidal neovascular vessels and/or the retinal neovascular vessels has reached its peak value under the irradiation of the laser light at 790 nm-wavelength; and the estimated time point is a time point when it is also observed by the fluorescence ocular fundus angiography apparatus or fluorescence microscope for funduscopy that the infrared fluorescence as emitted from the indocyanine green still remaining in the vascular walls of the retinal normal vascular vessels has disappeared completely even under the irradiation of the laser light at 790 nm-wavelength, and wherein at the estimated time point, said step (e) is initiated.

25. A method according to claim 22, wherein the laser light of 664 nm-wavelength, which is irradiated to the targeted lesions comprising the neovascular vessels in the ocular fundus, has an irradiance of 10 to 1500 $mW/cm^2$, on the top retina face, as measured at the corneal surface by means of an optical power meter, and said laser light of 664 nm-wavelength is irradiated for a duration of 10 to 300 seconds and at a fluence of the laser light in a range of 7.0 $J/cm^2$ to 250 $J/cm^2$, provided that said fluence of the laser light is evaluated by multiplying the laser irradiance (in $W/cm^2$) by the duration of the laser irradiation (in seconds), and wherein the lower is the dose of mono-L-aspartyl chlorin e6, the fluence of the laser light of 664 nm to be irradiated is controlled to be the higher, so as to achieve the selective occlusion of the neovascular vessels present in the targeted lesions.

26. A method according to claim 22, wherein the laser light of 664 nm-wavelength is started in the step (e) of the method to be irradiated at such a time point when a time period of 20 to 70 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 0.5 mg/kg to 10.0 mg/kg (as calculated on the weight basis of NPe6), and wherein the fluence of the laser light of 664 nm-wavelength to be irradiated is controlled within a range of 7 $J/cm^2$ to 205 $J/cm^2$.

27. A method according to claim 22, wherein the laser light of 664 nm-wavelength is started in the step (e) of the method to be irradiated at such a time point when a time period of 20 to 30 minutes has lapsed after the time of the intravenous administration of mono-L-aspartyl chlorin e6 or a salt thereof, particularly mono-L-aspartyl chlorin e6 tetra-sodium salt, as long as the chlorin e6 compound is given at a dose of 0.5 mg/kg to 0.9 mg/kg (as calculated on the weight basis of NPe6), and wherein the fluence of the laser light of 664 nm-wavelength to be irradiated is controlled within a range of 175 $J/cm^2$ to 205 $J/cm^2$.

28. A method according to claim 22, wherein the laser light of 664 nm-wavelength is started in the step (e) of the method to be irradiated at such a time point when a time period of 30 to 60 minutes has lapsed after the time of the intravenous administration of mono-L-aspartyl chlorin e6 or a salt thereof, as long as the chlorin e6 compound is given at a dose of 1 mg/kg to 1.9 mg/kg (as calculated on the weight basis of NPe6), and wherein the fluence of the laser light of 664 nm-wavelength to be irradiated is controlled within a range of 30 $J/cm^2$ to 175 $J/cm^2$.

29. A method according to claim 22, wherein the laser light of 664 nm-wavelength is started in the step (e) of the method to be irradiated at such a time point when a time period of 60 minutes has lapsed after the time of the intravenous administration of mono-L-aspartyl chlorin e6 or a salt thereof, as long as the chlorin e6 compound is given at a dose of 2 mg/kg to 9.5 mg/kg (as calculated on the weight basis of NPe6), and wherein the fluence of the laser light of 664 nm-wavelength to be irradiated is controlled within a range of 30 $J/cm^2$ to 45 $J/cm^2$.

30. A method according to claim 22, wherein the laser light of 664 nm-wavelength is started in the step (e) of the method to be irradiated at such a time point when a time period of 60 to 70 minutes has lapsed after the time of the intravenous administration of mono-L-aspartyl chlorin e6 or a salt thereof, as long as the chlorin e6 compound is given at a dose of 9.5 mg/kg to 10 mg/kg (as calculated on the weight basis of NPe6), and wherein the fluence of the laser light of 664 nm-wavelength to be irradiated is controlled within a range of 7 $J/cm^2$ to 9 $J/cm^2$.

31. A method according to claim 22, wherein the mammalian animal to be treated is a human having suffered from age-related macular degeneration with the choroidal neovascular vessels.

32. A method according to claim 22, wherein the mammalian animal to be treated is a human having suffered from proliferative diabetic retinitis with proliferative neovascular vessels in the retina.

33. The photodynamic therapy method of claim 1, wherein the chlorin e6 compound comprises mono-L-aspartyl chlorin e6 tetra-sodium salt.

34. The method of claim 12 wherein the chlorin e6 compound comprises mono-L-aspartyl chlorin e6 tetra-sodium salt.

35. The method of claim 22 wherein the chlorin e6 compound comprises mono-L-aspartyl chlorin e6 tetra-sodium salt.

36. The method of claim 1 wherein in said step (d) the estimated time point is determined as the time when it is observed that the intensity of the red fluorescence emitted from the photosensitizer has decreased to ⅓-fold or less.

37. The method of claim 12 wherein in said step (d), the estimated time is determined as the time point when it is observed that the intensity of the infrared fluorescence emitted from the indocyanine green has decreased to ⅓ fold or less in intensity.

38. The method of claim 22 wherein in said step (d), the estimated time period is a time point when it is observed that the intensity of infrared fluorescence emitted from the indocyanine green has decreased to ⅓-fold or less in intensity.

* * * * *